(12) United States Patent  
Clark

(10) Patent No.: US 9,797,844 B2  
(45) Date of Patent: Oct. 24, 2017

(54) CHEMICAL INDICATOR ELEMENT SYSTEMS FOR AQUATIC ENVIRONMENT WATER PARAMETER TESTING

(71) Applicant: Step Ahead Innovations, Inc., South Burlington, VT (US)

(72) Inventor: James E. Clark, South Burlington, VT (US)

(73) Assignee: Step Ahead Innovations, Inc., South Burlington, VT (US)

( * ) Notice: Subject to any disclaimer, the term of this patent is extended or adjusted under 35 U.S.C. 154(b) by 0 days.

(21) Appl. No.: 14/959,073

(22) Filed: Dec. 4, 2015

(65) Prior Publication Data

US 2016/0091432 A1    Mar. 31, 2016

Related U.S. Application Data

(63) Continuation of application No. PCT/US2014/043205, filed on Jun. 19, 2014.
(Continued)

(51) Int. Cl.
*G01N 21/77* (2006.01)
*A61K 36/185* (2006.01)
(Continued)

(52) U.S. Cl.
CPC ........... *G01N 21/77* (2013.01); *A61K 36/185* (2013.01); *G01N 21/274* (2013.01);
(Continued)

(58) Field of Classification Search
CPC ....... G01N 21/77; G01N 21/78; G01N 21/643
See application file for complete search history.

(56) References Cited

U.S. PATENT DOCUMENTS 3,794,814 A    2/1974  Lay et al.
3,850,752 A    11/1974 Schuurs et al.
(Continued)

FOREIGN PATENT DOCUMENTS

EP    1182445 A2    2/2002
EP     852715 B1    5/2002
(Continued)

OTHER PUBLICATIONS

Photonic BioSystems. Oxygen Sensing Overview. http://www.photonicsystems.com/oxygen.html. Accessed on Jul. 12, 2012.
(Continued)

*Primary Examiner* — Sam P Siefke
(74) *Attorney, Agent, or Firm* — Birch Tree IP Law & Strategy PLLC; Jamie T. Gallagher

(57) ABSTRACT

A chemical indicator element for use in an aquatic environment water parameter testing system. The chemical indicator element includes a chemical indicator and a thin film material having particular optical characteristics tied to the light from a light source, such as a light source of an optical reader element of a water parameter testing system. The chemical indicator element may also include at least one of a backing material that absorbs one or more wavelengths of the light of the light source and a holder including a material that absorbs one or more wavelengths of the light of the light source.

20 Claims, 23 Drawing Sheets

Related U.S. Application Data

(60) Provisional application No. 61/837,154, filed on Jun. 19, 2013.

(51) Int. Cl.
  *G06Q 30/02*     (2012.01)
  *G01N 21/27*     (2006.01)
  *G01N 21/64*     (2006.01)
  *G01N 27/06*     (2006.01)
  *G01N 21/85*     (2006.01)
  *G01N 33/18*     (2006.01)
  G01N 21/78      (2006.01)

(52) U.S. Cl.
  CPC ....... *G01N 21/643* (2013.01); *G01N 21/6428* (2013.01); *G01N 21/8507* (2013.01); *G01N 27/06* (2013.01); *G01N 33/18* (2013.01); *G06Q 30/0282* (2013.01); *G01N 21/78* (2013.01); *G01N 2021/6439* (2013.01); *G01N 2201/062* (2013.01); *G01N 2201/127* (2013.01); *G01N 2201/1211* (2013.01)

(56) References Cited

U.S. PATENT DOCUMENTS

| | | | |
|---|---|---|---|
| 3,964,831 | A | 6/1976 | Frank |
| 4,033,871 | A | 7/1977 | Wall |
| 4,138,669 | A | 2/1979 | Edison et al. |
| 4,205,043 | A | 5/1980 | Esch et al. |
| 4,418,037 | A | 11/1983 | Katsuyama et al. |
| 4,577,109 | A | 3/1986 | Hirschfeld |
| 4,652,137 | A | 3/1987 | Calzi |
| 4,743,558 | A | 5/1988 | Guigan |
| 4,785,814 | A | 11/1988 | Kane |
| 4,814,144 | A | 3/1989 | Edelmann et al. |
| 4,898,832 | A | 2/1990 | Klose et al. |
| 5,061,381 | A | 10/1991 | Burd |
| 5,110,724 | A | 5/1992 | Hewett |
| 5,122,284 | A | 6/1992 | Braynin et al. |
| 5,173,193 | A | 12/1992 | Schembri |
| 5,176,882 | A | 1/1993 | Gray et al. |
| 5,304,348 | A | 4/1994 | Burd et al. |
| 5,350,694 | A | 9/1994 | Zimmerle |
| 5,411,889 | A | 5/1995 | Hoots et al. |
| 5,504,714 | A | 4/1996 | Shonting |
| 5,508,200 | A | 4/1996 | Tiffany et al. |
| 5,511,547 | A | 4/1996 | Markle et al. |
| 5,547,578 | A | 8/1996 | Nielsen |
| 5,623,561 | A | 4/1997 | Hartman |
| 5,824,270 | A | 10/1998 | Rao |
| 5,895,565 | A | 4/1999 | Steininger et al. |
| 5,902,749 | A | 5/1999 | Lichtwardt et al. |
| 5,952,491 | A | 9/1999 | Leiner et al. |
| 5,958,782 | A | 9/1999 | Bentsen et al. |
| 5,976,888 | A | 11/1999 | Lee et al. |
| 5,994,150 | A | 11/1999 | Challener et al. |
| 6,002,475 | A | 12/1999 | Boyd et al. |
| 6,028,830 | A | 2/2000 | Fritsch et al. |
| 6,051,437 | A | 4/2000 | Luo et al. |
| 6,113,858 | A | 9/2000 | Tang et al. |
| 6,124,135 | A | 9/2000 | Leiner et al. |
| 6,171,866 | B1 | 1/2001 | He et al. |
| 6,187,530 | B1 | 2/2001 | Scholin et al. |
| 6,211,359 | B1 | 4/2001 | He et al. |
| 6,277,653 | B1 | 8/2001 | Challener et al. |
| 6,332,110 | B1 | 12/2001 | Wolfe |
| 6,340,431 | B2 | 1/2002 | Khan |
| 6,342,349 | B1 | 1/2002 | Virtanen |
| 6,360,182 | B1 | 3/2002 | Hales |
| 6,441,055 | B1 | 8/2002 | Katerkamp et al. |
| 6,535,795 | B1 | 3/2003 | Schroeder et al. |
| 6,553,319 | B1 | 4/2003 | Helffrich et al. |
| 6,560,543 | B2 | 5/2003 | Wolfe et al. |
| 6,576,474 | B2 | 6/2003 | Wallach |
| 6,599,748 | B1 | 7/2003 | Nakajima et al. |
| 6,625,824 | B1 | 9/2003 | Lutz et al. |
| 6,635,439 | B2 | 10/2003 | Morrison et al. |
| 6,653,152 | B2 | 11/2003 | Challener et al. |
| 6,657,546 | B2 | 12/2003 | Navarro et al. |
| 6,707,554 | B1 | 3/2004 | Miltner et al. |
| 6,756,014 | B2 | 6/2004 | Himmelhaus et al. |
| 6,794,191 | B2 | 9/2004 | Putnam et al. |
| 6,839,636 | B1 | 1/2005 | Sunshine et al. |
| 6,847,451 | B2 | 1/2005 | Pugh |
| 6,954,701 | B2 | 10/2005 | Wolfe |
| 7,014,612 | B2 | 3/2006 | Hubbard et al. |
| 7,040,157 | B2 | 5/2006 | Glasgow, Jr. et al. |
| 7,167,087 | B2 | 1/2007 | Corrington et al. |
| 7,222,047 | B2 | 5/2007 | McMillan et al. |
| 7,242,001 | B1 | 7/2007 | Hedges et al. |
| 7,283,245 | B2 | 10/2007 | Xiao et al. |
| 7,360,402 | B2 | 4/2008 | Liao |
| 7,378,954 | B2 | 5/2008 | Wendt |
| 7,385,497 | B2 | 6/2008 | Golden |
| 7,390,399 | B2 | 6/2008 | Dennis, II et al. |
| 7,391,333 | B2 | 6/2008 | Madden et al. |
| 7,393,188 | B2 | 7/2008 | Lawyer et al. |
| 7,454,295 | B2 | 11/2008 | Wolfe |
| 7,491,546 | B2 | 2/2009 | Jaunakais |
| 7,569,186 | B2 | 8/2009 | Bedingham et al. |
| 7,592,184 | B2 | 9/2009 | Khalil et al. |
| 7,601,544 | B2 | 10/2009 | Rehm |
| 7,720,615 | B2 | 5/2010 | Kim |
| 7,790,113 | B2 | 9/2010 | Putnam et al. |
| 7,858,383 | B2 | 12/2010 | He et al. |
| 7,862,770 | B2 | 1/2011 | Shahriari |
| 7,897,109 | B2 | 3/2011 | Labuda et al. |
| 7,905,245 | B2 | 3/2011 | McQuade et al. |
| 7,910,361 | B2 | 3/2011 | Barnes et al. |
| 7,924,927 | B1 | 4/2011 | Boesjes |
| 7,960,181 | B2 | 6/2011 | He et al. |
| 8,038,937 | B2 | 10/2011 | Kelly et al. |
| 8,038,947 | B2 | 10/2011 | Thompson |
| 8,062,221 | B2 | 11/2011 | Debreczeny et al. |
| 8,065,023 | B2 | 11/2011 | Graves |
| 8,069,706 | B2 | 12/2011 | Battefeld et al. |
| 8,097,725 | B2 | 1/2012 | He et al. |
| 8,125,331 | B2 | 2/2012 | Allen et al. |
| 8,145,431 | B2 | 3/2012 | Kloepfer et al. |
| 8,158,259 | B2 | 4/2012 | Ramamurthy et al. |
| 8,173,438 | B1 | 5/2012 | Putnam et al. |
| 8,202,503 | B2 | 6/2012 | Putnam et al. |
| 8,237,920 | B2 | 8/2012 | Jones et al. |
| 8,302,346 | B2 | 11/2012 | Hunt et al. |
| 8,455,844 | B2 | 6/2013 | Lear et al. |
| 8,510,064 | B2 | 8/2013 | Streppel et al. |
| 8,515,880 | B2 | 8/2013 | Holley et al. |
| 8,577,623 | B2 | 11/2013 | Wolfe |
| 8,586,911 | B2 | 11/2013 | Micinski et al. |
| 8,734,734 | B2 | 5/2014 | Kido et al. |
| 8,797,523 | B2 | 8/2014 | Clark |
| 8,828,728 | B2 | 9/2014 | Clark |
| 8,883,079 | B2 | 11/2014 | Clark |
| 8,968,681 | B2 | 3/2015 | Putnam et al. |
| 9,023,281 | B2 | 5/2015 | Clark |
| 9,261,462 | B2 | 2/2016 | Clark |
| 9,494,526 | B2 | 11/2016 | Clark |
| 9,494,527 | B2 | 11/2016 | Clark |
| 2001/0031503 | A1 | 10/2001 | Challener et al. |
| 2002/0054288 | A1 | 5/2002 | Kim et al. |
| 2002/0077777 | A1 | 6/2002 | Wolfe et al. |
| 2002/0117430 | A1 | 8/2002 | Navarro et al. |
| 2002/0119508 | A1 | 8/2002 | Morrison et al. |
| 2002/0123155 | A1 | 9/2002 | Himmelhaus et al. |
| 2002/0132363 | A1 | 9/2002 | Rehm |
| 2003/0003589 | A1 | 1/2003 | Khalil et al. |
| 2003/0003593 | A1 | 1/2003 | Wallach |
| 2003/0008400 | A1 | 1/2003 | Putnam et al. |
| 2003/0037602 | A1 | 2/2003 | Glasgow, Jr. et al. |
| 2003/0206302 | A1 | 11/2003 | Pugh |
| 2004/0006513 | A1 | 1/2004 | Wolfe |
| 2004/0013570 | A1 | 1/2004 | Labuda et al. |
| 2004/0077965 | A1 | 4/2004 | Hubbard et al. |

(56) References Cited

U.S. PATENT DOCUMENTS

| | | |
|---|---|---|
| 2004/0109853 A1 | 6/2004 | McDaniel |
| 2004/0138840 A1 | 7/2004 | Wolfe |
| 2004/0197922 A1 | 10/2004 | Cooper |
| 2004/0224351 A1 | 11/2004 | Shinohara |
| 2005/0112772 A1 | 5/2005 | Farone et al. |
| 2005/0157304 A1 | 7/2005 | Xiao et al. |
| 2005/0172910 A1 | 8/2005 | McMillan et al. |
| 2005/0180890 A1 | 8/2005 | Bedingham et al. |
| 2005/0214161 A1 | 9/2005 | Gupta |
| 2006/0051874 A1 | 3/2006 | Reed et al. |
| 2006/0073603 A1 | 4/2006 | Jaunakais |
| 2006/0092008 A1 | 5/2006 | Corrington et al. |
| 2006/0121623 A1 | 6/2006 | He et al. |
| 2006/0131245 A1 | 6/2006 | Dennis, II et al. |
| 2006/0210412 A1 | 9/2006 | Lawyer et al. |
| 2006/0222567 A1 | 10/2006 | Kloepfer et al. |
| 2006/0240573 A1 | 10/2006 | Kao et al. |
| 2006/0278093 A1 | 12/2006 | Biderman et al. |
| 2007/0039379 A1 | 2/2007 | Liao |
| 2007/0074758 A1 | 4/2007 | McQuade et al. |
| 2007/0078307 A1 | 4/2007 | Debreczeny et al. |
| 2007/0233397 A1 | 10/2007 | Kim |
| 2007/0241261 A1 | 10/2007 | Wendt |
| 2007/0241881 A1 | 10/2007 | Golden |
| 2007/0251461 A1 | 11/2007 | Reichard et al. |
| 2007/0257806 A1 | 11/2007 | Madden et al. |
| 2007/0259438 A1 | 11/2007 | He et al. |
| 2007/0259443 A1 | 11/2007 | He et al. |
| 2007/0259444 A1 | 11/2007 | He et al. |
| 2008/0012577 A1 | 1/2008 | Potyrailo et al. |
| 2008/0076184 A1 | 3/2008 | Putnam et al. |
| 2008/0152864 A1 | 6/2008 | Ramamurthy et al. |
| 2008/0160502 A1 | 7/2008 | Barnes et al. |
| 2008/0254544 A1 | 10/2008 | Modzelewski et al. |
| 2009/0004747 A1 | 1/2009 | Agree et al. |
| 2009/0028756 A1 | 1/2009 | Shahriari |
| 2009/0041621 A1 | 2/2009 | Kelly et al. |
| 2009/0042311 A1 | 2/2009 | Thompson |
| 2009/0139456 A1 | 6/2009 | Lin |
| 2009/0215183 A1 | 8/2009 | Takehara et al. |
| 2009/0301175 A1 | 12/2009 | Battefeld et al. |
| 2010/0024526 A1 | 2/2010 | Colvin, Jr. et al. |
| 2010/0052892 A1 | 3/2010 | Allen et al. |
| 2010/0069891 A1 | 3/2010 | Ginggen |
| 2010/0099193 A1 | 4/2010 | Hsu et al. |
| 2010/0129852 A1 | 5/2010 | Putnam et al. |
| 2010/0133175 A1 | 6/2010 | Putnam et al. |
| 2010/0136608 A1 | 6/2010 | Putnam et al. |
| 2010/0187185 A1 | 7/2010 | Johnson et al. |
| 2010/0228505 A1 | 9/2010 | Streppel et al. |
| 2010/0230614 A1 | 9/2010 | Lear et al. |
| 2010/0265509 A1 | 10/2010 | Jones et al. |
| 2010/0280773 A1 | 11/2010 | Saether |
| 2010/0330692 A1 | 12/2010 | Khalil et al. |
| 2010/0332149 A1 | 12/2010 | Scholpp |
| 2011/0071966 A1 | 3/2011 | Holley et al. |
| 2011/0081728 A1 | 4/2011 | Putnam et al. |
| 2011/0086359 A1* | 4/2011 | Babu .................. C12Q 1/6834 435/6.19 |
| 2011/0168609 A1 | 7/2011 | McQuade et al. |
| 2011/0179706 A1 | 7/2011 | Hunt et al. |
| 2011/0198487 A1 | 8/2011 | Micinski et al. |
| 2011/0218655 A1 | 9/2011 | Graves |
| 2011/0299130 A1 | 12/2011 | Ito |
| 2012/0092131 A1 | 4/2012 | Vasic et al. |
| 2012/0116683 A1 | 5/2012 | Potyrailo et al. |
| 2012/0183984 A1 | 7/2012 | He et al. |
| 2013/0009781 A1 | 1/2013 | Wolfe |
| 2013/0013259 A1 | 1/2013 | Wolfe |
| 2013/0168327 A1 | 7/2013 | Clark |
| 2014/0000507 A1 | 1/2014 | Clark |
| 2014/0000651 A1 | 1/2014 | Clark |
| 2014/0001126 A1 | 1/2014 | Clark |
| 2014/0016122 A1 | 1/2014 | Clark |
| 2014/0016344 A1 | 1/2014 | Clark |
| 2014/0017143 A1 | 1/2014 | Clark |
| 2014/0017796 A1 | 1/2014 | Clark |
| 2014/0017801 A1 | 1/2014 | Clark |
| 2014/0019060 A1 | 1/2014 | Clark |
| 2014/0019069 A1 | 1/2014 | Clark |
| 2014/0072474 A1 | 3/2014 | Kido et al. |
| 2014/0134052 A1 | 5/2014 | Stevenson et al. |
| 2016/0091431 A1 | 3/2016 | Clark |
| 2016/0091432 A1 | 3/2016 | Clark |
| 2016/0116418 A1 | 4/2016 | Clark |
| 2016/0200601 A1 | 7/2016 | Clark |

FOREIGN PATENT DOCUMENTS

| | | |
|---|---|---|
| EP | 1217373 A1 | 6/2002 |
| EP | 1225442 A2 | 7/2002 |
| EP | 1359409 A2 | 11/2003 |
| GB | 2480301 A | 11/2011 |
| GB | 2482155 A | 1/2012 |
| SG | 11201507067Q | 6/2016 |
| SG | 11201509863 R | 10/2016 |
| WO | 97/12225 | 4/1997 |
| WO | 2007/115321 A2 | 10/2007 |
| WO | 2013/090407 A2 | 6/2013 |
| WO | PCT/US2012/069209 | 6/2013 |
| WO | 2014/145337 A2 | 9/2014 |
| WO | PCT/US2014/030077 | 10/2014 |
| WO | PCT/US2014/043205 | 10/2014 |
| WO | 2014/205230 A1 | 12/2014 |

OTHER PUBLICATIONS

Photonic BioSystems. Oxygen Sensing Features and Benefits. http://www.photonicsystems.com/O2features.html. Accessed on Jul. 12, 2012.

Photonic BioSystems. Oxygen Sensing Applications. http://www.photonicsystems.com/O2applications.html. Accessed on Jul. 12, 2012.

Sutron. DS5x Multiparameter Water Quality Sonde Datasheet. http://www.sutron.conn/documents/ds5x-multiparameter-water-quality-sonde-datasheet.pdf. Accessed on Jul. 19, 2012.

Michael, Eric. EcoTech Marine Pump Patent Challenged: Request for Re-Examination Filed. GlassboxDesign.com. http://glassbox-design.com/2011/ecotech-marine-patent-reexam/. Sep. 4, 2011.

Pacific Sentry. Ammonia Detection Sensors/Monitors for Water Applications. http://www.pacificsentry.com/water.html. Accessed on Jul. 1, 2013.

Sutron. DS5x Multiparameter Water Quality Sonde Datasheet. Jun. 1, 2012.

Seneye. Retail Brochure for Aquatic Warning System. http://www.seneye.com. Accessed Jul. 11, 2012.

Gupta, B.D. et al. "A Long-Range Fiber Optic pH Sensor Prepared by Dye Doped Sol-Gel Immobilization Technique." Optics Communications 154 (1998) 282-284. Sep. 15, 1998.

Lamotte Spinlab Quick Guide. Dec. 10, 2012.

Lamotte Spinlab Announcement. http://www.lamotte.com/component/option. Feb. 2, 2012. Accessed using web.archive.org on Oct. 25, 2013.

Raghuraman, B. et al. "Spectroscopic pH Measurement for High Temperatures, Pressures and Ionic Strength." Wiley InterScience (www.interscience.wiley.com). Jul. 25, 2006.

Millero, F.J. "History of the equation of state of seawater." Oceanography 23(3):18-33, doi:10.5670/oceanog.2010.21. Sep. 2010.

Clayton, Tonya D. et al. "Spectrophotometric seawater pH measurements: total hydrogen ion concentration scale calibration of m-cresol purple and at-sea results." Deep-Sea Research, vol. 40, No. 10, pp. 2115-2129, 1993.

Millero, F.J. "Carbonate constants for estuarine waters." Marine and Freshwater Research, 2010, 61, 139-142. 2010.

Riddle, Dana. "Product Review: Inexpensive Analytical Devices: Hanna Instruments' Checkers: Alkalinity and Phosphate." Advanced Aquarist. Http://www.advancedaquarist.com/2011/8/review. Aug. 2011. Accessed on May 28, 2017.

(56) References Cited

OTHER PUBLICATIONS

Hanna Checker Product Review. Reef Addicts. http://www.reefaddicts.com/content.php/398-product-review-hanna-phosphate-checker. Oct. 26, 2013. Accessed May 28, 2017.
U.S. Appl. No. 13/713,495, dated Dec. 31, 2014, Notice of Allowance.
U.S. Appl. No. 13/713,495, dated Jan. 6, 2015, Amendment After Notice of Allowance (Rule 312).
U.S. Appl. No. 13/713,495, dated Jan. 20, 2015, Response to Amendment Under Rule 312.
U.S. Appl. No. 13/713,537, dated Dec. 3, 2013, Office Action.
U.S. Appl. No. 13/713,537, dated Apr. 3, 2014, Response to Office Action.
U.S. Appl. No. 13/713,537, dated Jun. 30, 2014, Examiner Initiated Interview Summary.
U.S. Appl. No. 13/713,537, dated Jun. 30, 2014, Notice of Allowance.
U.S. Appl. No. 13/713,537, dated Jul. 10, 2014, Amendment After Notice of Allowance (Rule 312).
U.S. Appl. No. 13/713,537, dated Oct. 22, 2014, Issue Notification.
U.S. Appl. No. 13/713,568, dated May 29, 2015, Office Action.
U.S. Appl. No. 13/713,568, dated Aug. 31, 2015, Response to Office Action.
U.S. Appl. No. 13/713,568, dated Nov. 27, 2015, Office Action.
U.S. Appl. No. 13/713,568, dated Feb. 27, 2016, Response to Office Action.
U.S. Appl. No. 13/713,568, dated Aug. 18, 2016, Office Action (Final).
U.S. Appl. No. 13/713,595, dated Jan. 16, 2015, Restriction Requirement.
U.S. Appl. No. 13/713,595, dated Mar. 16, 2015, Response to Restriction Requirement.
U.S. Appl. No. 13/713,595, dated Jun. 24, 2015, Office Action.
U.S. Appl. No. 13/713,595, dated Nov. 23, 2015, Response to Office Action.
U.S. Appl. No. 13/713,595, dated Mar. 3, 2016, Office Action (Final).
U.S. Appl. No. 13/713,595, dated Jul. 4, 2016, Response to Office Action.
U.S. Appl. No. 13/713,595, dated Jul. 21, 2016, Notice of Allowance.
U.S. Appl. No. 13/713,629, dated Jan. 28, 2014, Office Action.
U.S. Appl. No. 13/713,629, dated Apr. 28, 2014, Response to Office Action.
U.S. Appl. No. 13/713,629, dated Jul. 10, 2014, Supplemental Amendment.
U.S. Appl. No. 13/713,629, dated Jul. 16, 2014, Notice of Allowance.
U.S. Appl. No. 13/713,629, dated Aug. 20, 2014, Issue Notification.
U.S. Appl. No. 13/713,668, dated May 22, 2014, Notice of Allowance.
U.S. Appl. No. 13/713,668, dated Jun. 24, 2014, Notice to File Corrected Application Papers (After Allowance).
U.S. Appl. No. 13/713,668, dated Jul. 1, 2014, Amendment After Notice of Allowance (Rule 312).
U.S. Appl. No. 13/713,668, dated Jul. 16, 2014, Issue Notification.
U.S. Appl. No. 13/713,714, dated Feb. 17, 2015, Office Action.
U.S. Appl. No. 13/713,714, dated May 28, 2015, Response to Office Action.
U.S. Appl. No. 13/713,714, dated Aug. 18, 2015, Final Office Action.
U.S. Appl. No. 13/713,714, dated Dec. 18, 2015, Response to Office Action.
U.S. Appl. No. 13/713,714, dated Jan. 12, 2016, Applicant Initiated Interview Summary.
U.S. Appl. No. 13/713,714, dated Feb. 9, 2016, Advisory Action.
U.S. Appl. No. 13/713,737, dated Jul. 20, 2015, Office Action.
U.S. Appl. No. 13/713,737, dated Dec. 21, 2015, Response to Office Action.
U.S. Appl. No. 13/713,737, dated Mar. 18, 2016, Office Action (Final).
U.S. Appl. No. 13/713,773, dated Oct. 9, 2015, Notice of Allowance.
U.S. Appl. No. 13/713,773, dated Jan. 28, 2016, Issue Notification.
U.S. Appl. No. 13/713,818, dated Jan. 24, 2014, Office Action.
U.S. Appl. No. 13/713,864, dated Mar. 7, 2016, Restriction Requirement.
U.S. Appl. No. 13/713,864, dated May 9, 2016, Response to Restriction Requirement.
U.S. Appl. No. 13/713,864, dated Jul. 11, 2016, Notice of Allowance.
U.S. Appl. No. 14/959,063, dated Jun. 29, 2016, Office Action.
U.S. Appl. No. 14/959,063, dated Sep. 29, 2016, Response to Office Action.
U.S. Appl. No. 14/959,063, dated Nov. 3, 2016, Restriction Requirement.
U.S. Appl. No. 14/959,063, dated Jan. 3, 2017, Response to Restriction Requirement.
U.S. Appl. No. 14/959,063, dated Feb. 14, 2017, Notice of Allowance.
U.S. Appl. No. 14/959,063, dated May 15, 2017, Request for Continued Examination.
U.S. Appl. No. 14/895,980, dated May 30, 2017, Terminal Disclaimer.
U.S. Appl. No. 14/895,980, dated Jun. 6, 2017, Notice of Allowance and Examiner Interview Summary.
U.S. Appl. No. 13/713,568, filed Dec. 13, 2013.
U.S. Appl. No. 13/713,714, filed Dec. 13, 2013.
U.S. Appl. No. 13/713,737, filed Dec. 13, 2013.
U.S. Appl. No. 13/713,818, filed Dec. 13, 2013.
U.S. Appl. No. 14/771,491, filed Aug. 29, 2015.
U.S. Appl. No. 15/445,453, filed Feb. 28, 2017.
"Flourescence Spectroscopy." Wikipedia.org. Dec. 5, 2011. Accessed at Internet Archive Wayback Machine on Jun. 2, 2017 (http://web.archive.org/web/20111205222128/https://en.wikipedia.org/wiki/Fluorescence_spectroscopy).
U.S. Appl. No. 14/895,980, filed Dec. 4, 2015.
U.S. Appl. No. 14/959,063, filed Dec. 4, 2015.
eTerminal Disclaimer for U.S. Appl. No. 14/959,063, dated Jun. 6, 2017.
Office Action for U.S. Appl. No. 14/959,063, dated Jun. 16, 2017.

\* cited by examiner

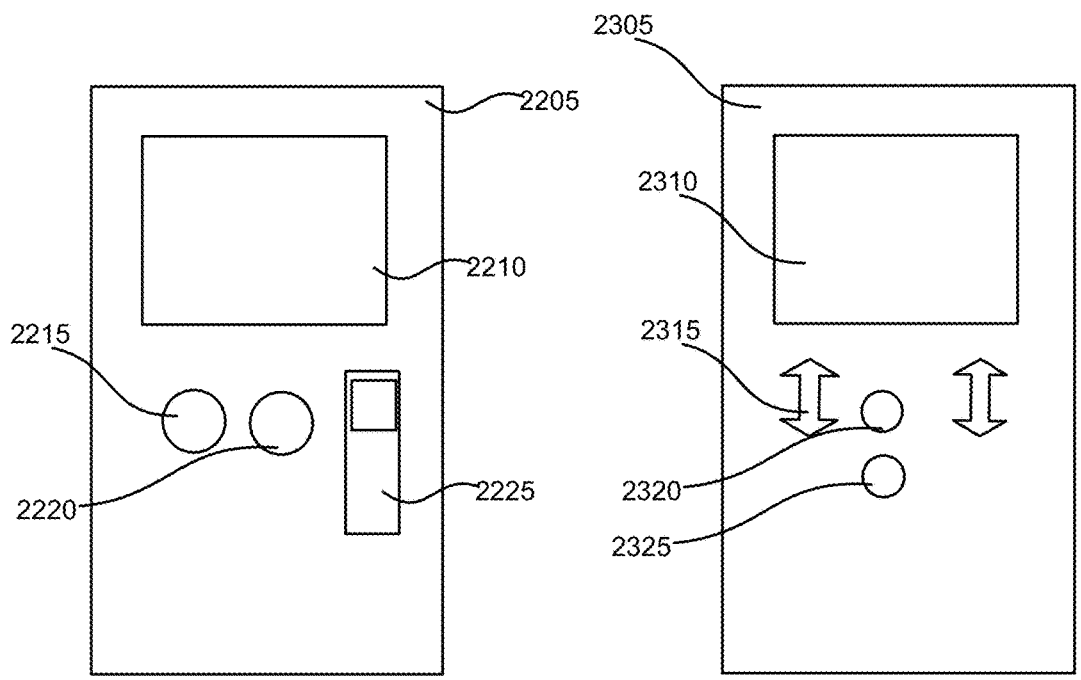
FIG. 22
FIG. 23
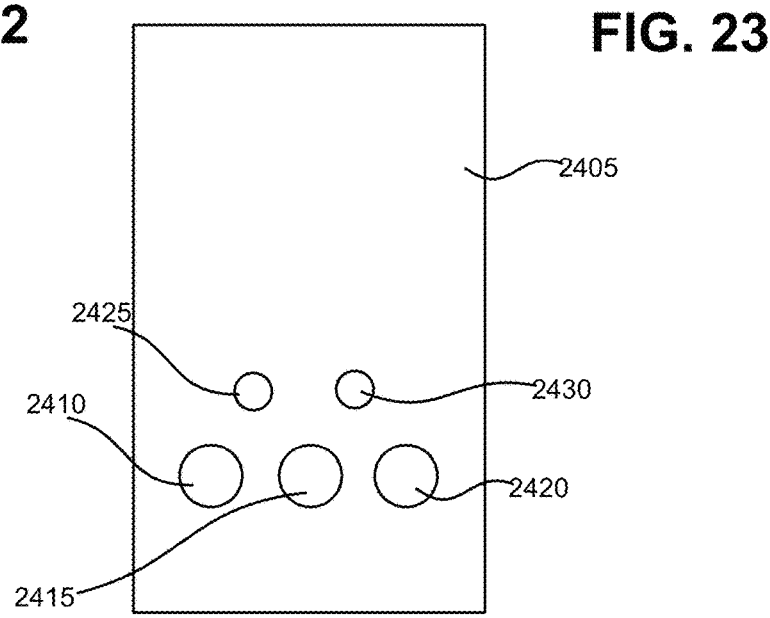
FIG. 24

CHEMICAL INDICATOR ELEMENT SYSTEMS FOR AQUATIC ENVIRONMENT WATER PARAMETER TESTING

RELATED APPLICATION DATA

This application is a continuation application of International Application No. PCT/US2014/043205, filed Jun. 19, 2014, entitled "Aquatic Environment Water Parameter Testing Systems and Methods," which application claims the benefit of priority of U.S. Provisional Patent Application Ser. No. 61/837,154, filed on Jun. 19, 2013, and titled "Aquatic Environment Water Parameter Testing Systems and Methods," each application incorporated by reference herein in its entirety.

This application is also related to commonly-owned U.S. patent application Ser. No. 13/713,495, entitled "Submersible Chemical Indicator Apparatuses For Use In Aquatic-Environment Monitoring/Measuring System;" and U.S. patent application Ser. No. 13/713,537, entitled "Aquatic Environment Water-Quality Monitor Having a Submersible Chemical Indicator Wheel;" and U.S. patent application Ser. No. 13/713,568, entitled "Embedded Indicator Dye Monitoring System and Method for An Aquatic Environment;" and U.S. patent application Ser. No. 13/713,595, entitled "Combined Illuminator/Light Collectors For Optical Readers;" and U.S. patent application Ser. No. 13/713,629, entitled "Dosage Protection System and Method For An Aquatic Environment;" and U.S. patent application Ser. No. 13/713,668, entitled "Chemical Indicator Obstruction Detection System and Method For An Aquatic Environment;" and U.S. patent application Ser. No. 13/713,714, entitled "Rate of Change Protection System and Method for an Aquatic Environment;" and U.S. patent application Ser. No. 13/713,737, entitled "Monitoring of Photo-Aging of Light-Based Chemical Indicators Using Cumulative Exposure Tracking, and Systems, Methods, Apparatuses, and Software Relating Thereto;" and U.S. patent application Ser. No. 13/713,773, entitled "Monitoring of Photo-Aging of Light-Based Chemical Indicators Using Illumination-Brightness Differential Scheme, and Systems, Methods, Apparatuses, and Software Relating Thereto;" and U.S. patent application Ser. No. 13/713,818, entitled "Assisted Dosing of Aquatic Environments For Maintaining Water Quality Therein, and Systems, Methods, Apparatuses, and Software Relating Thereto;" and U.S. patent application Ser. No. 13/713,864, entitled "Optical Reader Optic Cleaning Systems Having Motion Deployed Cleaning Elements, and Methods of Cleaning An Optical Reader Optic," each of which is filed on the same day as this application: Dec. 13, 2012, each of which is incorporated by reference herein in its entirety.

FIELD OF INVENTION

The present invention generally relates to the field of water quality management, such as for fish and coral aquariums, swimming pools, and hot tubs, among other aquatic environments. In particular, the present invention is directed to chemical indicator element systems and methods for aquatic environment water parameter testing.

BRIEF DESCRIPTION OF THE DRAWINGS

For the purpose of illustrating the invention, the drawing show aspects of one or more embodiments of the invention. However, it should be understood that the present invention is not limited to the precise arrangements and instrumentalities shown in the drawings, wherein:

FIG. 22 illustrates one example of a user interface on an outer portion of an electronics portion of an aquatic environment water parameter testing system;

FIG. 23 illustrates another example of a user interface on an outer portion of an electronics portion of an aquatic environment water parameter testing system;

FIG. 24 illustrates an exemplary surface of an electronics portion that in use comes into contact with a sample chamber;

SUMMARY OF THE DISCLOSURE

Figure 1:
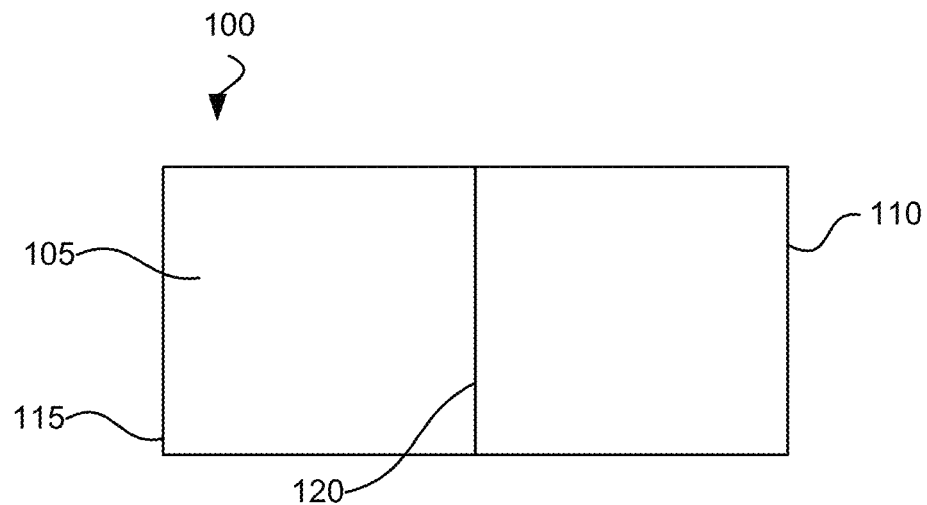
FIG. 1 illustrates a high level diagrammatic representation of one exemplary embodiment of an aquatic environment water parameter testing system.

In one implementation, a chemical indicator element for use in an aquatic environment water parameter testing system having a light source capable of generating an excitation energy and a light sensor for detecting light is provided. The chemical indicator element includes a chemical indicator responsive to a first excitation energy to generate a first emitted energy in response to the first excitation energy; and a thin film material having a first side and a second side, the chemical indicator associated with the first side, the thin film material being configured to: absorb and/or allow transmission of one or more wavelengths of light of the first excitation energy, and reflect one or more wavelengths of light of the first emitted energy; and at least one additional structural feature selected from the group consisting of: a backing material, the backing material positioned adjacent the second side of the thin film material, the backing material being a material that absorbs one or more wavelengths of light of the first excitation energy; a holder positioned adjacent the second side of the thin film material, the holder including a material that absorbs one or more wavelengths of light of the first excitation energy; and any combination thereof.

In another implementation, a chemical indicator element for use in an aquatic environment water parameter testing system having a light source capable of generating an excitation energy and a light sensor for detecting light is provided. The chemical indicator element includes a chemical indicator responsive to a first excitation energy to generate a first emitted energy in response to the first excitation energy; and a thin film material having a first side and a second side, the chemical indicator associated with the first side, the thin film material being configured to: absorb and/or allow transmission of one or more wavelengths of light of the first excitation energy, and reflect one or more wavelengths of light of the first emitted energy; and a backing material, the backing material positioned adjacent the second side of the thin film material, the backing material being a material that absorbs one or more wavelengths of light of the first excitation energy.

In yet another implementation, a chemical indicator element for use in an aquatic environment water parameter testing system having a light source capable of generating an excitation energy and a light sensor for detecting light is provided. The chemical indicator element includes a chemical indicator responsive to a first excitation energy to generate a first emitted energy in response to the first excitation energy; and a thin film material having a first side and a second side, the chemical indicator associated with the first side, the thin film material being configured to: absorb and/or allow transmission of one or more wavelengths of light of the first excitation energy, and reflect one or more wavelengths of light of the first emitted energy; and a holder positioned adjacent the second side of the thin film material, the holder including a material that absorbs one or

DETAILED DESCRIPTION

An aquatic environment water parameter testing device, various possible features thereof, and methods for implementing measurements in an aquatic environment are disclosed. Before describing several exemplary water quality monitoring systems, the term "aquatic environment" is defined, for example, to give the reader a sense of the wide applicability of the systems, apparatuses, methods, and software disclosed herein. As used herein and in the appended claims, "aquatic environment" shall mean any environment wherein water is present and for which it is desired to measure at least one parameter indicative of a quality of the water. In turn, "quality" is measured by the presence, absence, and/or amount of one or more chemicals, including minerals, in the water, and/or the presence, absence, and/or amount of one or more other materials, such as organic matter, inorganic particles, bacteria, etc., in the water, and any combination thereof. Examples of aquatic environments include, but are not limited to: aquariums, including aquarium sumps and aquarium plumbing; swimming/diving/wave pools, including swimming/diving/wave pool plumbing; hot tubs, including hot tub plumbing; fish ponds, including fish pond plumbing; potable water supplies, including plumbing therefor; sewage treatment infrastructure; water fountains; water displays; lakes and lagoons, and control structures and plumbing therefor (such as at amusement parks and other facilities having highly controlled environments); and food processing facilities that use water, for example, to wash food items, cook food items, transport food items, to name just a few. Those skilled in the art will certainly be able to think of other examples of aquatic environments for which teachings of the present disclosure will be pertinent. In this connection, while many of the examples herein are directed to aquarium set ups for keeping fish, coral, and/or other aquatic life, skilled artisans will readily be able to adapt the fundamental teachings herein to virtually any other aquatic environment wherein water quality measurement is desired.

FIG. 1 illustrates a high level diagrammatic representation of one exemplary embodiment of an aquatic environment water parameter testing system 100. Testing system 100 includes an electronics portion 105 and a sample chamber portion 110. As will be discussed in greater detail below with respect to multiple examples, electronics portion 105 includes one or more electronic and/or hardware elements associated with the operation of testing system 100. Example electronic and hardware elements that may be included with electronics portion 105 include, but are not limited to, a processor element, a user interface (e.g., a display element, a user input element), an optical reader element, a memory (e.g., including instructions for operating one or more of the functions of testing system 100), a user access element (e.g., a wireless network element, a wired network element, fiber optic, IR emitter), a removable memory device (e.g., a memory card slot/reader), a temperature measurement element, a conductivity measurement element, a water agitation element, a power supply, signal conditioning element, a chemical indicator element identification device, a universal serial bus and port, and any combinations thereof.

Electronics portion 105 includes a housing 115 for enclosing one or more of the electronic and/or hardware elements of electronics portion 105. Housing 115 may be constructed of any suitable material. Example materials for housing include, but are not limited to, ABS plastic, acrylic, stainless steel, and any combinations thereof. Housing 115 may be constructed to allow for protection against water entering the housing (e.g., the housing may be waterproofed).

As will also be discussed in greater detail below with respect to multiple examples, sample chamber portion 110 includes one or more wall structures that form at least a part of a chamber for holding a sample of water to be tested using testing system 100. Sample chamber portion 110 also includes an opening (not shown) for allowing the sample of water to be placed into the sample chamber. Example ways to place a sample of water in the sample chamber include, but are not limited to, submersing fully or partially testing system 100 in the water to be sampled allowing a sample of the water to enter an opening in sample chamber portion 110, scooping a sample of water using the testing system into an opening in sample chamber portion 110, using a cup or other vessel to transfer a sample of water into an opening in sample chamber portion 110, using a syringe to transfer a sample of water into an opening in sample chamber portion 110, using a pump to transfer a sample of water into an opening in sample chamber portion 110, and any combinations thereof.

A cover may also be included for the opening. Such a cover may perform any of a variety of functions. Example functions for a cover include, but are not limited to, sealing the sample chamber to prevent spillage of the sample of water, blocking light from entering the sample chamber, thermal stability, and any combinations thereof. Additional details regarding covers and openings for water sample placement are discussed below (e.g., with respect to the aquatic environment water parameter testing systems shown in FIGS. 25A, 25B, 26A, and 26B).

In one example, an outer surface 120 of housing 115 may be exposed to the sample chamber such that outer surface 120 forms a portion of the boundary of the sample chamber. Examples with this feature are discussed further below.

Sample chamber portion 110 also includes a chemical indicator element that includes a chemical indicator. A chemical indicator may work in conjunction with light output from an optical reader element of electronics portion 105 to produce a detectable physical change that can be utilized to determine a value of a parameter for a water sample in the sample chamber.

Figure 2:
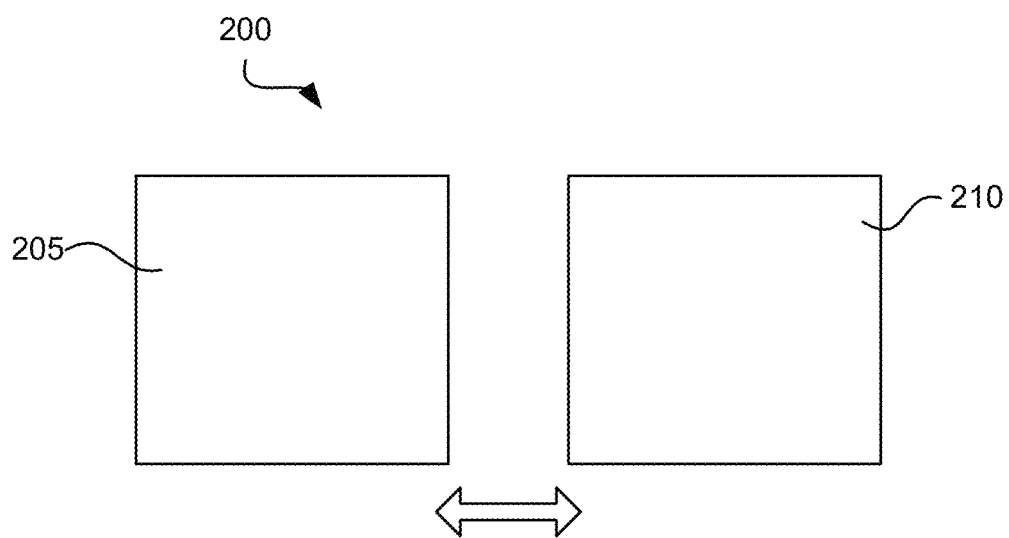
FIG. 2 illustrates a high level diagrammatic representation of another exemplary embodiment of a testing system.

Electronics portion 105 and sample chamber portion 110 are shown in FIG. 1 as being connected. In one example, electronics portion 105 and sample chamber portion 110 are configured as parts that are inseparable during normal usage (e.g., one or more portions of housing 115 may be contiguous with one or more portions of an outer housing of sample chamber portion 110). In another example, at least a part of sample chamber portion 110 is separable from electronics portion 105. In one such example, a chemical indicator element of sample chamber portion 110 is separable from testing system 100. FIG. 2 illustrates a high level diagrammatic representation of one exemplary embodiment of a testing system 200 in which at least a part 205 of a sample chamber portion is separable from remaining portions 210 (e.g., an electronics portion and part of a sample chamber portion) of testing system 200. Separation of a chemical indicator element may provide any of a variety of benefits. Example benefits that may be provided by a separable chemical indicator element include, but are not limited to, ability to change parameters to be tested using testing system 100, provision of access to clean portions of testing system 100 (e.g., an outer surface of an optical reader element of electronics portion 105, interior surfaces of a sample chamber, electrodes, etc.), replacement of aged chemical indicator material, calibration by user or factory, and any combinations thereof. Examples of ways to separate a chemical indicator element from testing system 100 are discussed further below. In one example, a removably connected chemical indicator element forms at least a part of one or more walls of a sample chamber portion (e.g., allowing the sample chamber portion to hold a liquid sample). In another example, a removably connected chemical indicator element connects with a sample chamber portion at an opening in the sample chamber portion such that when connected to the opening the chemical indicator element closes the opening.

Exemplary aspects and features of an aquatic environment water parameter testing system (such as systems 100, 200) and related methods are now discussed with respect to exemplary implementations illustrated in FIGS. 3 to 7 and additional figures following. Individual examples shown in the Figures may include one or more of the aspects and/or features. However, an aquatic environment water parameter testing system may include any combination of the aspects and/or features that may be discussed and shown separately. Details and examples of aspects and/or features will be discussed as they are presented in the example implementations and such details and examples can apply across all of the implementations discussed below.

As discussed above, an optical reader element (e.g., as part of an electronics portion) and a chemical indicator (as part of a chemical indicator element of a sample chamber portion) work in conjunction to determine a value for a water parameter. An aquatic environment water parameter testing system may test for one or more water parameters. Different aquatic environments may require different parameters to be measured. Such parameters may indicate a level of water quality, an amount of a constituent and/or property of a water sample, and/or other aspects of a water sample. As will be discussed further below, knowing the value of a water parameter may allow a user of a testing system to do one or more of a variety of tasks with such information. Example tasks include, but are not limited to, manually adjusting one or more chemical additives to an aquatic environment, providing a water parameter value to an automated system for automatedly adjusting one or more chemical additives to an aquatic environment, adjusting (e.g., manually or automatically) a temperature of an aquatic environment, providing a water parameter value to an online service (e.g., for informative or inquiry purposes), causing a trigger alarm device to provide an alarm to a user of an aquatic environment and/or an aquatic environment water parameter testing system according to the current disclosure, and any combinations thereof. Example water parameters include, but are not limited to, pH, Carbonate hardness, general hardness, conductivity, calcium content, magnesium content, dissolved oxygen ($O_2$) content, carbon dioxide content, ammonia content, phosphate content, nitrate content, nitrite content, iron content, and any combinations thereof. One or more parameters may be measured to determine a value of a different parameter. In one such example, multiple parameter values may be utilized in combination to determine another parameter value (e.g., measuring carbon dioxide and pH to calculate a value for Carbonate hardness).

Figure 3:
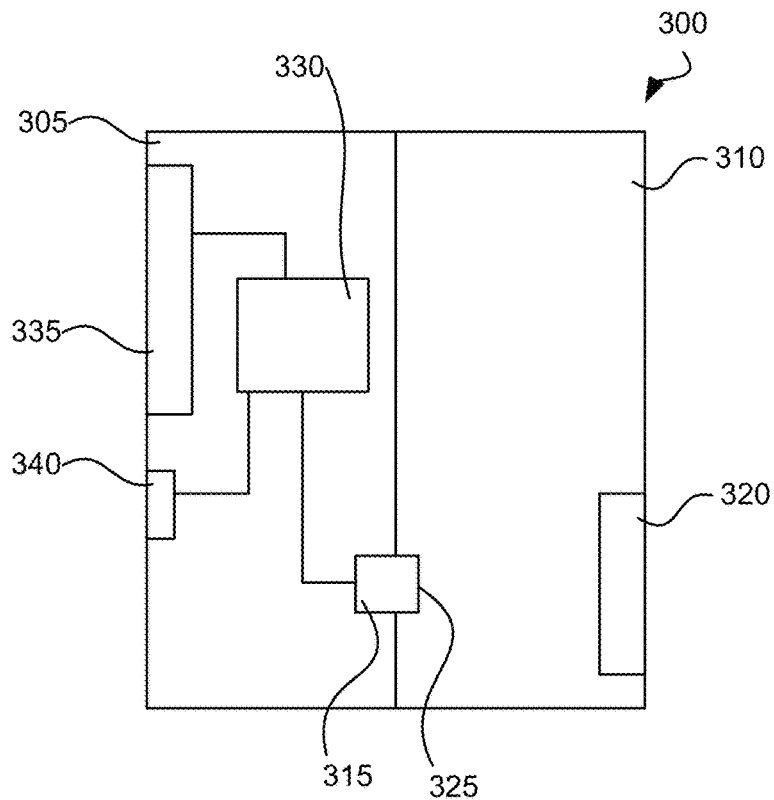
FIG. 3 illustrates yet another exemplary implementation of an aquatic environment water parameter testing system.

FIG. 3 illustrates one exemplary implementation of an aquatic environment water parameter testing system 300. Testing system 300 is shown as a cross section. It will be understood by those of ordinary skill that testing system 300 is a three dimensional structure. The structure can be of a variety of shapes, sizes, and configurations consistent with the disclosure herein. Testing system 300 includes an electronics portion 305 and a sample chamber portion 310. Electronics portion 305 includes an optical reader element 315 aligned with a chemical indicator element 320 of sample chamber portion 310. Sample chamber portion 310 includes an opening (not shown) for allowing placement of a sample of water to be tested into a sample chamber formed by the structural elements of sample chamber portion 310 (e.g., one or more walls of sample chamber portion 310, an outer surface of electronics portion 305, chemical indicator element 320, other elements of testing system 300, and any combinations thereof). Example locations for an opening in sample chamber portion (such as sample chamber portion 310) include, but are not limited to, in an upper surface/wall of the sample chamber portion, in a side surface/wall of the sample chamber portion, and any combinations thereof. A sample chamber portion may include more than one opening for allowing a sample to be added. Additionally, a sample chamber portion may include one or more openings to allow for a chemical indicator element to be attached to a sample chamber portion. Examples of such openings are discussed further below.

A chemical indicator element, such as chemical indicator element 320, includes one or more chemical indicators. A chemical indicator is a chemical structure that is designed and configured to be put into contact with a sample of water and which undergoes a detectable physical change as an amount of one or more constituents and/or properties that are part of the sample of water changes. Examples of a detectable physical change include, but are not limited to, a change in fluorescence intensity, fluorescence decay (e.g., lifetime fluorescence), phase fluorescence, change in electromagnetic energy absorbance (change in reflectivity), change in color (e.g., visible color, non-visible color), a change in fluorescence ratio between two or more wavelengths, and any combinations thereof. As discussed above, a chemical indicator may be used to determine one or more water parameters, examples and aspects of which are discussed above.

Chemical materials for a chemical indicator are vast and can be selected based on considerations of an aquatic environment to be tested, a parameter to be tested, a dynamic range of values of a constituent and/or property of the water to be tested, an illumination light source and wavelengths to be used as part of an optical reader element (e.g., where an excitation energy is required for fluorescence detectable physical change), temperature, salinity, and/or other considerations. In one example, a chemical indicator includes one or more indicator dyes (e.g., a fluorescent dye). In one such example, one or more indicator dyes are immobilized in a suitable medium. Example immobilization mediums include, but are not limited to, a gel, a polymer matrix (e.g., a cellulosic matrix), a hydrogel, a plastic (e.g., micro porous PTFE), and any combinations thereof. In one example, immobilization includes covalent bonding of a dye to cellulose fibers which in turn are immobilized in a medium, such as a hydrogel.

A chemical indicator may be submersible in water. In one example, a water submersible indicator is stable in water (e.g., an active indictor dye remains contained in a medium such that the indicator dye does not mix with and/or change the water into which it is submersed). A chemical indicator may be reversible (e.g., the chemical indicator returns to a previous physical condition as one or more parameters of a water sample change back to an original level).

In one example, chemical indicators for detecting calcium, magnesium, and/or carbon dioxide may be included with a chemical indicator element. Examples of a chemical indicator dye sensitive for calcium include, but are not limited to, a calcium detecting aminonaphthalimide, a calcium detecting perylenediamide, and any combination thereof. Examples of a chemical indicator dye sensitive for magnesium include, but are not limited to, a magnesium detecting dye based on a aminonaphthalimide, a magnesium detecting dye based on a photon induced electron transfer process (PET), a magnesium detecting dye based on a intramolecular charge transfer process (ICT), a magnesium detecting perylenediamide and any combinations thereof. Examples of a chemical indicator dye sensitive for carbon dioxide include, but are not limited to, a carbon dioxide sensitive dye based on a aminonaphthalimide, a carbon dioxide sensitive dye based on a photon induced electron transfer process (PET), a carbon dioxide sensitive dye based on a intramolecular charge transfer process (ICT), a carbon dioxide sensitive perylenediamide and any combinations thereof.

A chemical indicator element may also include one or more substrates onto which one or more chemical indicators are supported. In one example, a substrate may include a chemical indicator holder and/or a backing material. A chemical indicator holder may take a variety of shapes, sizes and/or configurations. Example considerations for determining a shape, size, and/or configuration for a chemical indicator holder include, but are not limited to, a shape, size, configuration of an opening in a sample chamber portion to which a chemical indicator element is to be connected; a shape, size, configuration of an attachment element of a sample chamber portion to which a chemical indicator element is to be attached; the size, configuration, and/or number of one or more chemical indicators to be supported; the size, configuration, and/or number of one or more optical reader elements utilized in conjunction with one or more chemical indicators supported by a chemical indicator holder; and any combinations thereof. Various examples of chemical indicator elements and holders are discussed further below (e.g., with respect to FIGS. 11 to 13 and 19 to 21).

Figure 8:
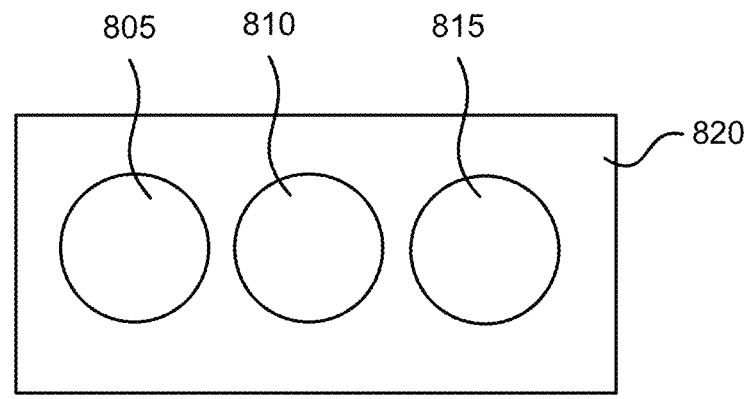
FIG. 8 illustrates an example chemical indicator element having examples of three circular chemical indicator patches.
Figure 9:
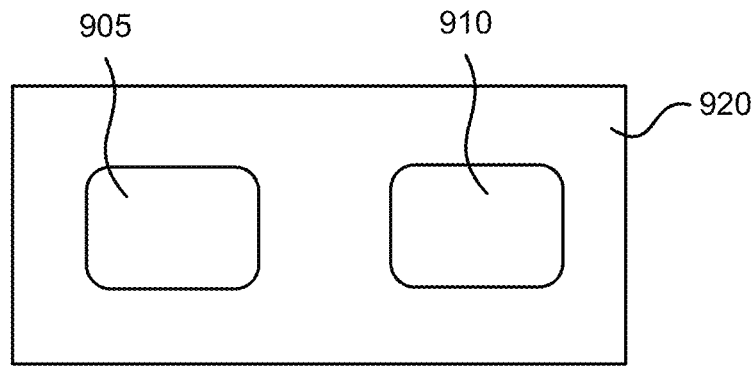
FIG. 9 illustrates example chemical indicator element having examples of two rounded rectangular chemical indicator patches.
Figure 10:
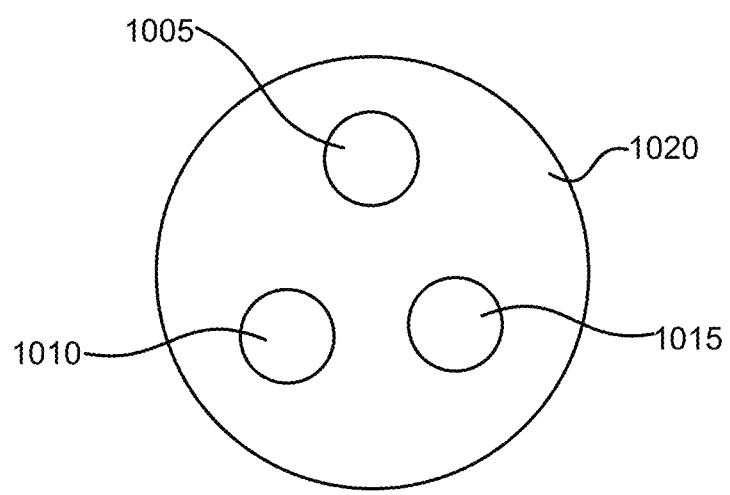
FIG. 10 illustrates an example chemical indicator element having examples of three circular chemical indicator patches

A chemical indicator may have any of a variety of shapes and configurations as part of a chemical indicator element of a sample chamber portion (such as portion 310). Example shapes for a chemical indicator include, but are not limited to, circular, rectangular, square, and any combinations thereof. A chemical indicator element may include any number of chemical indicators. FIGS. 8 to 10 illustrate exemplary configurations of chemical indicators of a chemical indicator element. FIG. 8 shows an example chemical indicator element having three circular chemical indicator patches 805, 810, 815 arranged in a linear fashion to each other. Chemical indicators 805, 810, 815 may be supported by a substrate 820. Substrate 820 may include a chemical indicator holder. FIG. 9 shows an example chemical indicator element having two rounded rectangular chemical indicator patches 905, 910 arranged side-by-side. Chemical indicators 905, 910 may be supported by a substrate 920. Substrate 920 may include a chemical indicator holder. FIG. 10 shows an example chemical indicator element having three circular chemical indicator patches 1005, 1010, 1015 arranged in a pattern. Chemical indicators 1005, 1010, 1015 may be supported by a substrate 1020. Substrate 1020 may include a chemical indicator holder.

A chemical indicator element may also include an information storage and communication element. An information storage and communication element stores one or more elements of information (e.g., information about a particular chemical indicator element) that can be communicated to an aquatic environment water parameter testing system. This may be important where an aquatic environment water parameter testing system is configured to have a removable and/or removably connected chemical indicator element. In one such example, the identity of one or more chemical indicators of a chemical indicator element may be stored in an information storage and communication element. Example information storage and communication elements include, but are not limited to, an RFID (Radio Frequency Identification) device, a bar code device, a QR code device, a magnetic storage element, one wire touch memory, and any combinations thereof. It is understood that a chemical indicator element may include a data storage component of an information storage and communication element and an electronics portion (such as portion 305) may include a reader portion of the information storage and communication element such that information can be stored on the chemical indicator element and read by the electronics portion. In one example, a chemical indicator element includes an RFID chip containing stored information and a corresponding electronics portion of an aquatic environment water parameter testing system includes a corresponding reader portion (e.g., a reader/writer device) for reading and/or writing information from/to the RFID chip on the chemical indicator element. Other devices can be used in place of an RFID chip and RFID reader device. Example information for storage on an identification element and/or communication to an aquatic environment water parameter testing system include, but are not limited to, a type of chemical indicator included as part of a chemical indicator element, calibration information for one or more chemical indicators included as part of a chemical indicator element, manufacturing information for one or more chemical indicators included as part of a chemical indicator element, chemical indicator element identification data, chemical indicator element usage data, an authentication key to thwart counterfeiting of a chemical indicator element, light exposure data for one or more chemical indicators, a serial number, a date of manufacture of a chemical indicator element, and any combinations thereof.

A chemical indicator element may include portions of one or more structural components (e.g., one or more walls) of a sample chamber portion (such as portion 310) of an aquatic environment water parameter testing system. In one example, one or more walls or other structural components of a sample chamber portion that form a sample chamber and hold a water sample may be part of a chemical indicator holder of a chemical indicator element. One such example is shown below with respect to FIG. 14. In such an example, a substantial amount of the structural elements that form a sample chamber portion may be part of a chemical indicator element that is removably connected to a corresponding electronics portion such that when the chemical indicator element is removed substantially only the electronics portion remains. In one exemplary aspect, an outer surface of an electronics portion may form one or more structural boundaries of a sample chamber into which a water sample may be placed. Other examples are discussed further below.

A chemical indicator element may include one or more attachment elements for attaching the chemical indicator element to a portion of a sample chamber portion (such as portion 310) and/or an electronics portion (such as portion 305). For a chemical indicator element that is not removable from an aquatic environment water parameter testing system, an attachment element may have a configuration that is not removable during normal use or is of a more permanent nature of connecting the chemical indicator element (e.g., one or more screws, glue, etc.). For a chemical indicator element that is removable from an aquatic environment water parameter testing system, an attachment element may include a configuration that allows a user to readily remove the chemical indicator element from, and reconnect it to the aquatic environment water parameter testing system. Example attachment elements include, but are not limited to, one or more screws, glue, a snap lock connector, a magnetic connector, a slide attachment connector, a form-in-place gasket, a toe-in snap connector, a threaded connector, and any combinations thereof. An aquatic environment water parameter testing system may include a corresponding connection element as part of an electronics portion and/or a portion of a sample chamber portion for receiving and/or mating with an attachment element of a chemical indicator element. For example, an opening in a sample chamber portion may include female threadings to accept and mate with a chemical indicator element having male threadings. In an example with rotational movement in mounting, a chemical indicator element may include markings for aligning one or more chemical indicators with one or more optical reader elements when the threading is mated. Such alignment marking may also be utilized in other configurations where alignment of a chemical indicator with an optical reader element may be assisted.

A removable chemical indicator element may include one or more water leakage prevention elements configured to minimize and/or prevent water from leaking via a connection of a chemical indicator element and an aquatic environment water parameter testing system. In one example a water leakage prevention element includes one or more gaskets configured to seal the chemical indicator element when connected to an aquatic environment water parameter testing system.

An optical reader element, such as optical reader element 315, includes an optical sensor for optically detecting a detectable physical change in one or more chemical indicators. A detectable physical change may be detectable based on light that reflects from, is absorbed by, and/or is emitted by a chemical indicator. For example, an amount and/or quality of a light reflected by, absorbed by, and/or emitted from a chemical indicator may represent an amount of a constituent and/or property of a water sample being tested. An optical sensor may be selected and configured based on a variety of considerations including, but not limited to, a type of light being detected from a chemical indicator (e.g., light having been absorbed by a chemical indicator, light having been emitted (such as via fluorescence) upon excitation of a chemical indicator, light reflected by a chemical indicator); a color of light (e.g. wavelength) of light being absorbed, reflected, and/or emitted by a chemical indicator; a quantity/amount of light being absorbed, reflected, and/or emitted by a chemical indicator; a shape, size, configuration of a chemical indicator; the aquatic environment from which a water sample is taken for testing; a type of chemical indicator; a parameter being measured by a chemical indicator; sensing distance; and any combination thereof. As used herein, the term "light" includes electromagnetic radiation of any wavelength from any region of the spectrum, including visible, ultraviolet, infrared, and others. Example optical sensors include, but are not limited to, a photodetector, a line camera, an array camera, a charge-coupled device-based sensor, a CMOS-based sensor, photodiode, and any combinations thereof. There are no limitations of the type and configuration of suitable optical sensors as long as they perform the requisite function(s) of a particular arrangement of an aquatic environment water parameter testing system.

In one exemplary aspect, an optical reader element is positioned such that an optical sensor is aligned and at a distance to receive light from a corresponding chemical indicator. As discussed above, a chemical indicator element may have more than one chemical indicator. In one such example, an optical reader element may include an optical sensor that is configured to receive and detect light from each of the multiple chemical indicators. In another such example, an optical reader element may include more than one optical sensor with each optical sensor configured to receive and detect light from a corresponding one or more of the multiple chemical indicators (e.g., each chemical indicator may have a corresponding optical sensor in an optical reader element). In another example, an electronics portion (e.g., portion 305) of an aquatic environment water parameter testing system may have more optical sensors than corresponding chemical indicators of a chemical indicator element. For example, a system with a removable chemical indicator element may allow chemical indicator elements with varying numbers of chemical indicators to be connected (e.g., with only those chemical indicators present at any given connection being read by a corresponding optical sensor). In a further example, an electronics portion (e.g., portion 305) of an aquatic environment water parameter testing system may have fewer optical sensors than corresponding chemical indicators of a chemical indicator element. In one such example, not all chemical indicators would have a corresponding optical sensor for detecting light therefrom. In another such example, one optical sensor may be configured to detect light from more than one chemical indicator. An electronics portion may also have more than one optical reader elements each with one or more optical sensors to correspond with one or more chemical indicators. More than one optical sensor of an optical reader element and/or more than one optical reader element may also be configured to receive and detect light from the same chemical indicator.

An optical reader element may include a light source element for providing a light to a chemical indicator. Light may, for example, be produced by a light source of an optical reader element and directed onto a chemical indicator of a chemical indicator element. Such light may be reflected by, absorbed by, and/or cause emission by a chemical indicator. In one example, light from one or more light source elements provides the light that is reflected by, absorbed by, and/or acts as an excitation energy for emission by one or more chemical indicators. In another example, ambient light and/or light from one or more light source elements provides the light that is reflected by, absorbed by, and/or acts as an excitation energy for emission by one or more chemical indicators. An optical reader element may include more than one light source. Also, an electronics portion (such as portion 310) may include more than one optical reader element. In one exemplary aspect, correspondence between one or more chemical indicators and one or more light source elements and/or one or more optical reader elements (as with the optical sensors) may be one-to-one, one-to-many, many-to-one, many-to-many, and/or another configuration. Example light source elements include, but are not limited to, a light emitting device (LED), a laser, an incandescent bulb, a fluorescent light source, and any combinations thereof. A light source element may include a filter configured to allow light generation of a desired/necessary spectral content. For example, a light source element may include an optical filter configured to allow transmission of light of a desired spectral content. In one such example a short pass filter with a wavelength of cutoff of approximately 510 nm (and longer) can be used to permit blue light from a source to reach the chemical sensor but eliminate light that would otherwise obscure or interfere with the reading of the emissions from the chemical sensor. Some blue LEDs typically emit spectral content as long as 700 nm and therefore a short pass filter can be used to limit the spectral content to desired wavelengths of light.

An optical reader element may include one or more optics (such as a lens) to assist with collecting light from one or more chemical indicators and/or transmitting light from one or more light source elements. An optic may also assist in directing light onto a desired portion of a chemical indicator. Example optics include, but are not limited to, an optical fiber, a lens, a light pipe, other optic elements, and any combinations thereof. Example optics and exemplary features and aspects are disclosed with respect to FIGS. 15 to 18 of U.S. patent application Ser. No. 13/713,495, entitled "Submersible Chemical Indicator Apparatuses For Use In Aquatic-Environment Monitoring/Measuring System," to James Clark, filed on Dec. 13, 2012, the disclosure of which and the disclosure of accompanying optical reader elements (also referred to as combined illuminator/light collectors therein) are each incorporated herein by reference in its entirety. Several such examples of optical reader elements and their features are shown below with respect to FIGS. 35 to 38.

An optical reader element may include a temperature sensor configured to detect a temperature of one or more of the optoelectrical circuits and/or components of the optical reader element. In one example, one or more of the optoelectrical circuits include one or more light sources (e.g., one or more LED's). Circuitry for temperature sensing will be understood to a person of ordinary skill. A temperature sensor may be positioned proximate to one or more circuits and/or other components for which a temperature measurement is desired. A temperature sensor may be connected to a processing element of an electronics portion (such as electronics portion 305). Processing elements are discussed further below and can be utilized to process temperature information (e.g., in correlation with one or more memory elements storing calibration and/or other information). In one example, a temperature of a component of an optical reader element (e.g., of an LED) can be utilized to calibrate for a measurement taken from a chemical indicator. For example, an illumination intensity of an LED may change with the temperature of the LED circuitry. In such an example, the amount of light directed to a chemical indicator may fluctuate with temperature of the LED such that the amount of light reflected, absorbed, and/or utilized as an excitation energy for fluorescence may also fluctuate. In one example, such fluctuation can be calibrated for by having known correlation information for a given LED and/or chemical indicator type as a function of temperature of the LED. In a further example, such fluctuation can be calibrated for by having known correlation information for a given LED as a function of the temperature of the LED. Another example of using temperature for calibration is discussed further below. An alternative to using a temperature sensor to determine the temperature of an LED includes measuring the forward voltage at a die junction of an LED when a precision current source (e.g., one with 10.00 milliamps) is utilized. The voltage can be correlated to a change in temperature of the LED via a calibration step. This calibration can be used to develop one or more coefficients of change in brightness percentage for an LED as a function of change in temperature.

One example of a temperature compensation involves an equation:

$$L = L_{25}(1+K)^{(T-25)}$$

where T is the current temperature of the light source (e.g., measured using a temperature sensor proximate the light source) in Celsius, $L_{25}$ is a value of expected light level from the light source of the optical reader element at 25 degrees Celsius (e.g., a value that can be measured and stored in a memory of an aquatic environment water parameter testing system), K is a temperature coefficient for the light source of the optical reader element (e.g., a value provided by manufacturer of light source, a value measured once the light source is part of the optical reader element, etc.) per degree Celsius (e.g., a value of 0.5%/degree Celsius, K=0.0005), and L is a computed value of light level that should come from a light source of an optical reader element at the current temperature of the light source. K values can also be stored in a memory of an aquatic environment water parameter testing system. In one example, a K value is a positive value indicating that as the temperature increases, the amount of light from the light source increases in level. In another example, a K value is a negative value indicating that as the temperature increases, the amount of light from the light source decreases in level. An increase/decrease in light level from a light source that is directed at a chemical indicator may produce a corresponding increase/decrease in light emitted from the chemical indicator. It is noted that a different reference temperature other than 25 degrees Celsius can be used as the reference for expected light level at a known temperature in place of the $L_{25}$ value.

A calibration value (such as the value L) can be used to correct an optical reading from an optical sensor of an optical reader element. For example, using values from the above example equation, the computed value L may be divided by the $L_{25}$ value to get a calibration value that can be multiplied by the value of the light detected by an optical sensor to correct the reading for the temperature of the light source. In one such example, the level of light from a light source at a particular temperature may be 80% of the light at 25 degrees Celsius (from $L/L_{25}$). Multiplying 80% by the value of the light detected at the optical sensor can give a corrected value for the optical reading. Other exemplary aspects and features of an optical reader element and its interaction with a chemical indicator, including multiple reading for error correction, multiple reading for data collection, reference illumination and data reading, and other aspects are disclosed in U.S. patent application Ser. No. 13/713,495, entitled "Submersible Chemical Indicator Apparatuses For Use In Aquatic-Environment Monitoring/Measuring System," to James Clark, filed on Dec. 13, 2012, the disclosure of which is incorporated herein by reference in its entirety.

Referring again to FIG. 3, optical reader element 315 is shown as part of electronics portion 305 with an exposed end 325 to allow for alignment of light from one or more chemical indicators of chemical indicator element 320 to one or more sensor elements and/or to allow for alignment of light illuminated from a light source element of optical reader element 315 to one or more chemical indicators of chemical indicator element 320. The exposed end 325 of optical reader element 315 comes into contact with water and constituents of the water from a sample placed in the sample chamber of sample chamber portion 310. Exposed end 325 is shown as extending from the wall of the electronics portion 305. In an alternative example, an optical reader element may be more flush with a wall of an electronics portion. This exposed end 325 may include one or more optics. Such optics may become dirty from debris and other matter within a water sample. Cleaning of an optical reader element may be achieved via removal of a removable chemical indicator element and/or via one or more other openings in a sample chamber portion (examples of such openings and removable chemical indicator elements are shown and discussed further below) to obtain access to the optical reader element. Optical reader element 315 and/or electronics portion 305 may include a water sealing to prevent water leakage from the sample chamber into electronics portion 305.

One or more of the components of optical reader element 315 are connected to a processing element 330. A processing element, such as processing element 330, includes one or more processors for controlling one or more operations of the components of an aquatic environment water parameter testing system. A processing element may also include, or be connected to, one or more memory elements. A memory element may include machine executable instructions for execution by a processing element for operating one or more components and/or performing any of the functionalities disclosed herein. A memory element may also include data associated with one or more functions of one or more components. Example operations for control by a processor element include, but are not limited to, control of components of an optical reader element, control of a temperature sensor and/or temperature regulator, calculation of calibration information, calculation of temperature values, control of a conductivity element, calculation of a conductivity value, control of a user interface, storage of information and/or data collected by a component of a an electronics portion, control of an information storage reader element (e.g., an RFID reader), control of stored information regarding one or more chemical indicator elements, pump, and any combinations thereof. Example memory elements include, but are not limited to, a cache memory, a random-access memory (RAM) (e.g., dynamic RAM, static RAM), a read-only memory, a removable hardware storage media (e.g., a magnetic storage device, an optical storage device, a flash memory device, etc.), and any combinations thereof. Example processors include, but are not limited to, an ARM processor, an AVR processor, an MSP430 processor, a DSP processor, and any combinations thereof.

Figure 11:
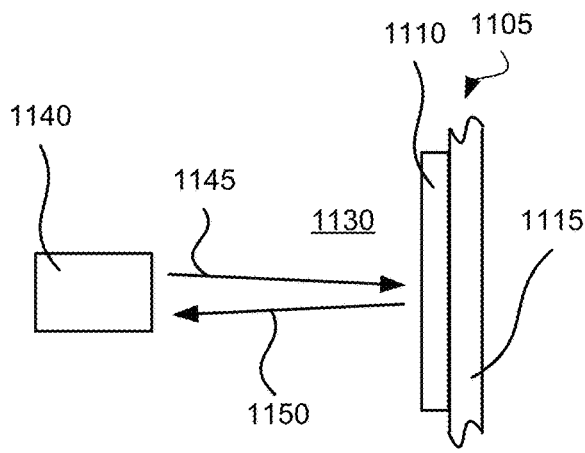
FIG. 11 illustrates an exemplary implementation of an optical reader element in relation to an exemplary implementation of a chemical indicator element.
Figure 12:
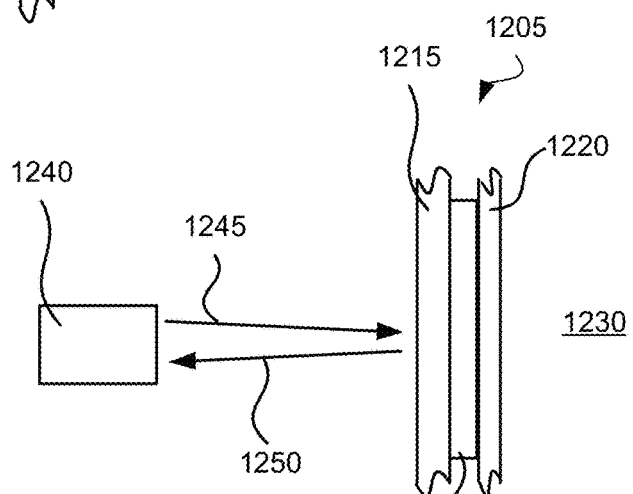
FIG. 12 illustrates another exemplary implementation of an optical reader element in relation to another exemplary implementation of a chemical indicator element.
Figure 13:
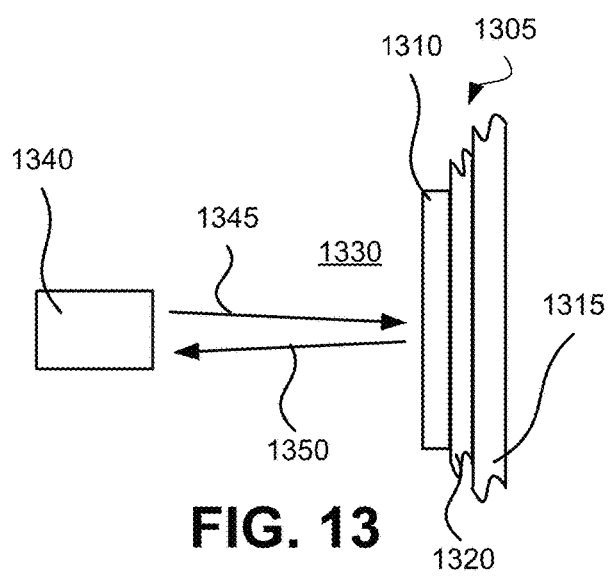
FIG. 13 illustrates yet another exemplary implementation of an optical reader element in relation to yet another exemplary implementation of a chemical indicator element.

FIGS. 11 to 13 illustrate exemplary implementations of an optical reader element in relation to exemplary implementations of a chemical indicator element. FIG. 11 illustrates an exemplary arrangement of a chemical indicator element 1105 including a chemical indicator 1110 on a holder 1115. In this example, chemical indicator 1110 is secured to holder 1115. With this configuration, chemical indicator 1110 is directly exposed to water 1130 for which the chemical indicator is designed for use. In one example of use, chemical indicator 1110 is illuminated by an optical reader element 1140 (e.g., having a light source and an optical sensor) with light 1145 and return light 1150 is collected therefrom by the optical reader element. FIG. 12 illustrates another exemplary arrangement of a chemical indicator element 1205 including a chemical indicator 1210 on a holder 1215. In this example, chemical indicator 1210 is secured to holder 1215, which in this example is transparent at least to the wavelength(s) of light necessary for the chemical indicator to be used as an optical indicator. Alternatively, if holder 1215 is generally opaque to a relevant wavelength(s), it can be provided with a suitable window (not shown) in the material of the holder 1215 that is transparent to the necessary wavelength(s). A light blocking backing 1220 that blocks light from the backside of holder 1215 is positioned adjacent chemical indicator 1205 between the chemical indicator and water 1230. Light blocking backing 1220 can be porous so as to allow water 1230 to reach chemical indicator 1210, since the opposite side of the chemical indicator is not in contact with the water because of holder 1215 and/or its window. In one example, light blocking backing 1220 can be a light blocking hydrogel, such as a carbon-containing hydrogel. In one example of use, chemical indicator 1210 is illuminated using an optical reader element 1240 by light 1245 and return light 1250 is collected therefrom by optical reader element 1240. FIG. 13 illustrates yet another exemplary arrangement of a chemical indicator element 1305 including a chemical indicator 1310 on a holder 1315. In this example, chemical indicator 1310 is secured to a backing material 1320. In one example, chemical indicator 1310 is an indicator dye embedded in a hydrogel which is bonded to backing material 1320, which can also be a hydrogel with a light blocking and/or absorbing material embedded therein (e.g., carbon fiber filaments, other light absorbing material). Backing material 1320 is attached to holder 1315. In one example, backing material 1320 is glued to holder 1315. Backing material 1320 can provide a variety of benefits. Examples of benefits provided by backing material 1320 in such a configuration include, but are not limited to, blocking light reflection from holder 1315, blocking light reflection from holder 1315, minimizing light passage from behind chemical indicator 1310, minimizing light scattering from behind chemical indicator 1310, and any combinations thereof. Chemical indicator 1310 is in contact with water 1330. In another exemplary aspect, this configuration of chemical indicator 1310, backing material 1320, and holder 1310 allows chemical indicator 1310 to be in direct contact with water 1330. Example benefits of this configuration include, but are not limited to, faster response time (e.g., indicator is in direct contact with water, such as in a hydrogel that is contacting water), allowing water sample to be between optical reader element and chemical indicator, any combination thereof. In one example of use, chemical indicator 1310 is illuminated using an optical reader element 1340 by light 1345 and return light 1350 is collected therefrom by optical reader element 1340.

Figure 31:
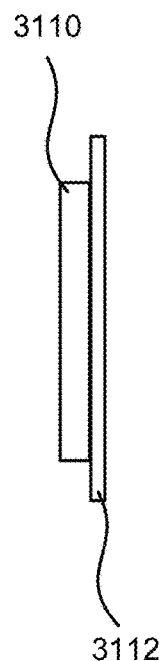
FIG. 31 illustrates an exemplary implementation of a chemical indicator.

A chemical indicator according to the implementations of various methods and systems disclosed herein may also be associated with a partially reflective, transmissive, and/or absorptive thin film material. In one exemplary aspect, a chemical indicator that emits light in response to an excitation light (e.g., an excitation light being illuminated by an optical reader element onto a fluorescent chemical indicator that emits a responsive light from which information about a component of a water sample can be determined) can be placed in proximity to a thin film material that absorbs or otherwise allow transmission of one or more of the wavelengths of light of the excitation light. FIG. 31 illustrates an exemplary implementation of a chemical indicator 3110 attached to a thin film material 3112. In this example, a water sample may come into contact with chemical indicator 3110 causing a measurable change in the chemical indicator 3110. In one such example, a water sample may be in direct contact on the same side as chemical indicator 3110. In another such example, a water sample may come into contact through thin film material 3112 (e.g., a thin film material that is porous to part or all of the water sample). A thin film material may be selected to have a reflective/transmissive/absorptive property designed to minimize excitation energy illuminated onto chemical indicator 3110 from reflecting to an optical reader that would detect that energy (e.g., to minimize noise from that excitation energy) and/or to maximize light emitted from chemical indicator 3110 being reflected to an optical reader that would detect the emitted light (e.g., to maximize signal strength of the detected emitted energy). Examples of a property for a thin film material include, but are not limited to, a property of absorbing one or more wavelengths of an excitation energy, transmitting one or more wavelengths of an excitation energy, reflecting one or more wavelengths of an emitted energy from a chemical indicator, and any combinations thereof. A chemical indicator/thin film material may be attached to a holder. A chemical indicator/thin film material may also be included with a backing material. A chemical indicator/thin film material may be part of a chemical indicator element.

Figure 32:
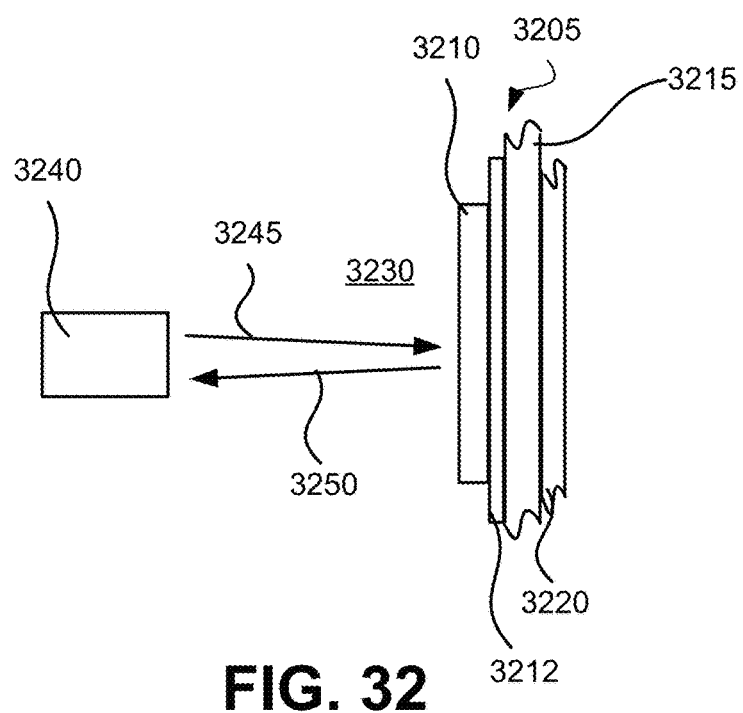
FIG. 32 illustrates another exemplary implementation of a chemical indicator element.

FIG. 32 illustrates another exemplary implementation of a chemical indicator element 3205 including a chemical indicator 3210 and a thin film material 3212. Thin film material 3212 is attached to an optional holder 3215. In one example, holder 3215 is constructed of an energy absorbing and/or non-reflective material, such as a black plastic. In another example, holder 3215 is constructed of a transparent material, such as a clear plastic. Holder 3215 may be backed by a backing material, such as backing 3220. Chemical indicator 3210 is directly exposed to water 3230 for which the chemical indicator is designed for use. In one example of use, chemical indicator 3210 is illuminated by an optical reader element 3240 (e.g., having a light source and an optical sensor) with light 3245 and return light 3250 is collected therefrom by the optical reader element. In one example of use, light 3245 causes a change in chemical indicator 3210 that produces light 3250, which is indicative of one or more components of water 3230. Light 3250 may emanate outwardly from chemical indicator 3210 with some of light 3250 directed toward thin film material 3212 and some directed toward optical reader 3240 to be detected. Additionally, in this example, some of light 3245 may pass through chemical indicator 3210. Thin film material 3212 may have one or more properties that minimize light 3245 bouncing back to optical reader 3240 and/or maximize light 3250 being directed to optical reader 3240. Examples of a property for thin film material 3212 include, but are not limited to, a property of absorbing one or more wavelengths of light 3245, transmitting one or more wavelengths of light 3245 (e.g., such that it does not reflect back to optical reader 3240), reflecting one or more wavelengths of light 3250 (e.g., such that it is redirected back to optical reader 3240), and any combinations thereof.

Figure 33:
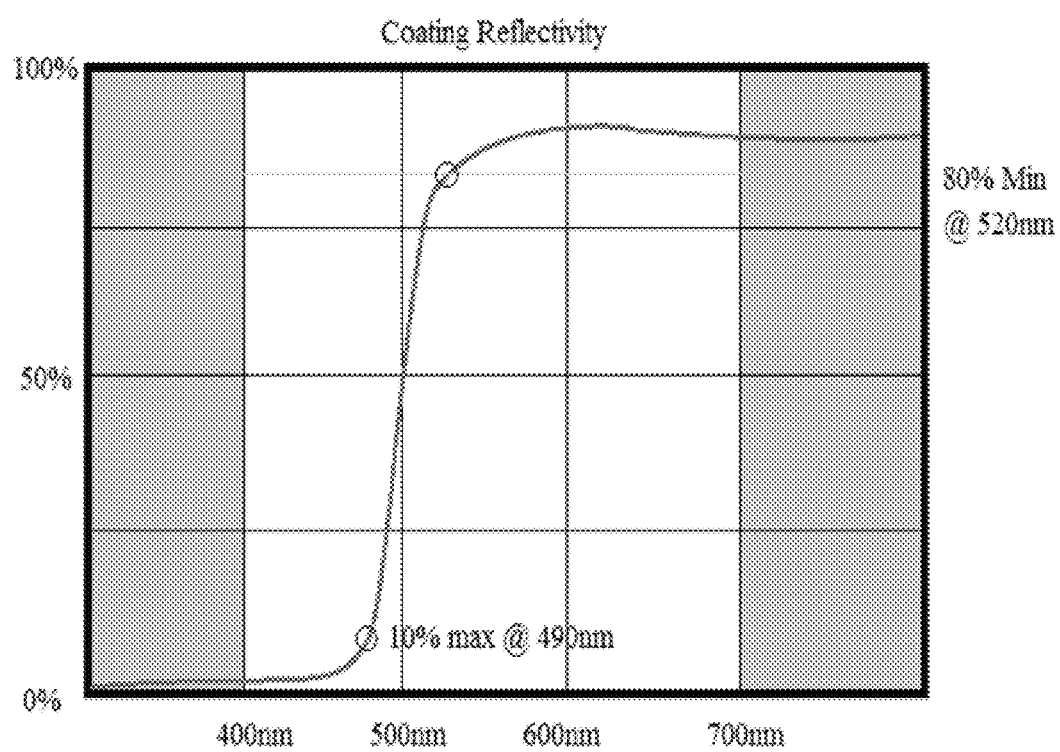
FIG. 33 illustrates one example thin film reflectivity plot for an exemplary implementation of a thin film material.

FIG. 33 illustrates one example thin film reflectivity plot for an exemplary implementation of a thin film material. The plot shows percent reflectivity of light at various wavelengths for an exemplary thin film material. In this example, a small percentage of light is reflected for wavelengths up to about 490 nm (nanometers) at which point about 10 percent is reflected. Above 490 nm reflectivity increases quickly up to an about 80 percent reflectivity at and above 520 nm. In one such example, an excitation energy of 470 nm would be transmitted through the thin film material and/or absorbed by the thin film material while allowing significant reflection of wavelengths above 520 nm. Such an example would be good for chemical indicators that emit responsive light at one or more wavelengths above 520 nm. Other alternative reflectivity profiles are also possible, such as with a narrow band of reflectivity at emitted wavelengths and/or a narrow band of absorption/transmission at excitation wavelengths.

Referring again to FIG. 3, electronics portion 305 also includes a user interface that includes a display 335 and a user input/output element 340, each connected to processing element 330. A user interface is configured to allow information from an electronics portion (such as electronics portion 305) to be presented to a user of an aquatic environment water parameter testing system. For example, detected and/or calculated parameter values from optical reader element interaction with one or more chemical indicators can be presented to a user. Other information may also be presented to a user. Examples of such information include, but are not limited to, a temperature value, a water constituent value, a conductivity value, a current time, a time remaining for an event of an aquatic environment water parameter testing system (e.g., a time required to allow a water sample to be in contact with one or more chemical indicators, a time until a data reading will be taken, a time until a data reading will be presented to a user, etc.), a value related to an age of a chemical indicator and/or chemical indicator element (e.g., using stored information from an RFID reading and a number of light illumination/sensor cycles to determine a remaining viable life of a chemical indicator), a type of chemical indicator connected to an aquatic environment water parameter testing system, a parameter being tested for, and any combinations thereof. In one example, a user interface may include a display device for communicating information to a user. Example display devices include, but are not limited to, a video display (e.g., a flat panel display (LCD, LED, OLED, etc.), a CRT display), a touch-screen display, an indicator light display, an audio display, a non-video flat panel display (e.g., LCD, LED, OLED, etc.), a gauge display, an analog indicator display, voice synthesis, and any combinations thereof.

A user interface may also be configured to allow a user to input or output information from an aquatic environment water parameter testing system. A user interface may include one or more user input/output elements. Example user input/output elements include, but are not limited to, a button, a dial, a touch sensitive device (e.g., a touchscreen), a toggle, a switch (e.g., a membrane switch, a physical switch), a conductive rubber device, a click wheel and/or dial, a contact snap button, a communications port, a network connection, a removable memory port (e.g., a flash memory card slot), a microphone, a cursor control device (e.g., a roller ball, a toggle, a mouse), a camera element, a keypad, a keyboard, optic touch sensor, and any combinations thereof. Examples of a communication port include, but are not limited to, a video out port (e.g., an HDMI port, a VGA port), a serial bus port (e.g., a USB port), a jack port (e.g., an RCA jack, a mini-jack), a network port, a FIREWIRE port, an ESATA port, SCSI, advanced technology attachment (ATA), serial ATA and any combinations thereof. Examples of a network connection include, but are not limited to, a LAN connection, an Internet connection, a wide area network connection, an Ethernet connection, a wired connection, a wireless connection, fiber optic, and any combinations thereof. An electronics portion (e.g., electronics portion 305) may include appropriate circuitry and processor connections (as well as, corresponding machine executable instructions in a memory) for operation of a user input/output element. In one example, a user input/output element may be utilized to output data detected and/or measured related to one or more water samples to a network and/or a computer device for sharing analyzing and/or sharing information about one or more water parameters. Examples of ways to utilize information in various networking, computing, and social networking environments are disclosed in U.S. patent application Ser. No. 13/713,495, entitled "Submersible Chemical Indicator Apparatuses For Use In Aquatic-Environment Monitoring/Measuring System," to James Clark, filed on Dec. 13, 2012, the disclosure of which is incorporated herein by reference in its entirety. In the disclosure therein, information about one or more parameters may be wirelessly transmitted from a water quality monitoring device to a network and/or computing device. In one example, information from an aquatic environment water parameter testing system of the current disclosure may be similarly wirelessly communicated and/or transferred to a network and/or computer device by another user input/output element (e.g., transferring data from an aquatic environment water parameter testing system to an flash memory card and then to a network and/or computer device).

An electronics portion (e.g., electronics portion 305) may also include a power source (not shown in FIG. 3). A power source may be configured to provide power to one or more of the components of an aquatic environment water parameter testing system of the present disclosure. Examples of a power source include, but are not limited to, a DC power source, an AC power source, a connection to a standard wall outlet, a battery, a solar panel, and any combinations thereof.

An electronics portion may include any circuitry and/or additional components that correspond with a particular power source to receive, harness, and/or deliver power from the power source to one or more components of an aquatic environment water parameter testing system.

An aquatic environment water parameter testing system may also include a sample temperature measurement element, a conductivity element, and/or a water agitation element. FIGS. 4 to 7 illustrate examples of such elements in exemplary aquatic environment water parameter testing systems. Each system may include any of the above components in any combinations whether or not explicitly discussed with each system. Similar components as discussed with respect to FIG. 3 and generally above have similar functionality and features, except where illustrated. As discussed above, the components, features and functionality of each as discussed throughout may be in any combination in an aquatic environment water parameter testing system. FIGS. 4 to 7 illustrate the features separately for exemplary purposes only.

Figure 4:
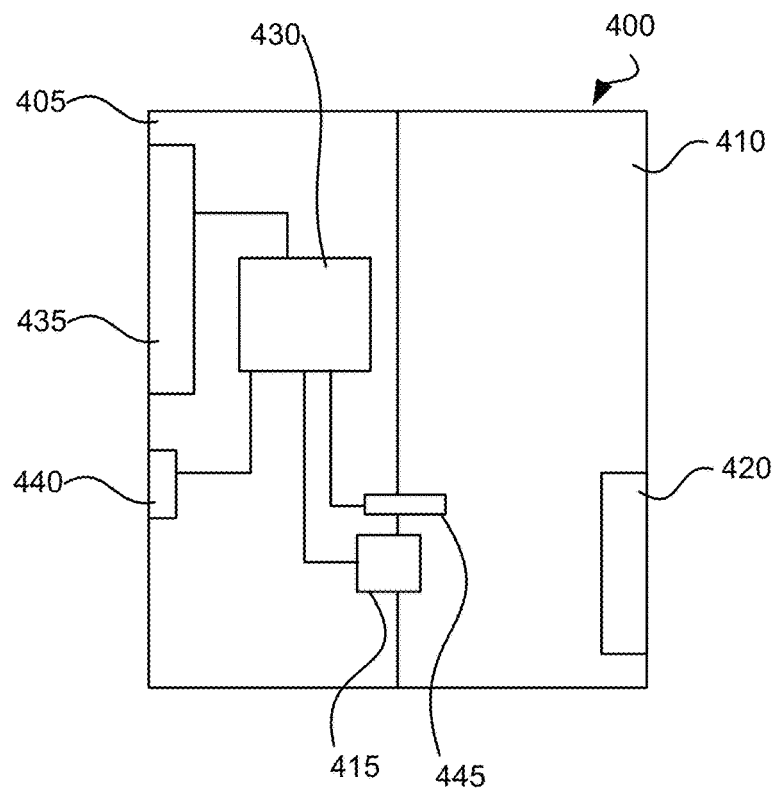
FIG. 4 illustrates an exemplary implementation of an aquatic environment water parameter testing system having an exemplary conductivity element.

FIG. 4 illustrates an exemplary implementation of an aquatic environment water parameter testing system 400. As with system 300, testing system 400 is shown as a cross section of a three dimensional structure. Testing system 400 includes an electronics portion 405 and a sample chamber portion 410. Electronics portion 405 includes an optical reader element 415 aligned with a chemical indicator element 420 of sample chamber portion 410. Sample chamber portion 410 includes an opening (not shown). Electronics portion 405 includes, a processor 430, and a user interface including a display element 435 and a user input/output element 440. Electronics portion 405 includes one or more conductivity elements 445. A conductivity element may include one or more conductivity electrode and any associated circuitry for providing a conductivity value to a processing element (e.g., processor element 430). Conductivity element 445 is shown connected to processor element 430 for providing communicating a conductivity value and/or data for use by processor element 430 for calculating a conductivity value. Example conductivity electrodes include, but are not limited to, a solid wire, a rod, a screw, and any combinations thereof. A conductivity electrode may be coated with a coating, such as a rhodium, platinum, and/or other platinum metal group coating. A coating may be of a suitable thickness for providing conductivity, protecting an electrode from corrosion, and/or another benefit. In one example, a coating of 2 micron or more is provided on one or more conductivity electrodes. As discussed above with respect to access to an optical reader element for cleaning, a provision for access to one or more conductivity electrodes for cleaning may also be made. In another example, one or more conductivity electrodes may be cleaned using an acid-based washing via one or more openings of a sample chamber portion of an aquatic environment water parameter testing system.

In one example, an electronics portion of an aquatic environment water parameter testing system includes two conductivity electrodes. In one such example, measuring a current between two conductivity electrodes exposed to a sample of water and also knowing a voltage applied across the two conductivity electrodes can allow calculation of a resistance. A processor, such as processor element 430 (and an associated memory element), can be configured to control the applied voltage or current determination for calculating resistance. From a resistance value, a conductivity value can be obtained (e.g., conductivity=1/resistance). In one example, a processor can control an AC pulsed signal across two conductivity electrodes reversing polarity with pulsing. In one exemplary aspect, such pulsing of polarity can possibly prevent ions from migrating to one of the electrodes and causing enhanced corrosion and/or error. A conductivity value of a water sample can be used to correct for one or more errors in a reading from a chemical indicator. Examples of such a correction are discussed below with respect to the methods of FIGS. 27 and 28.

Figure 5:
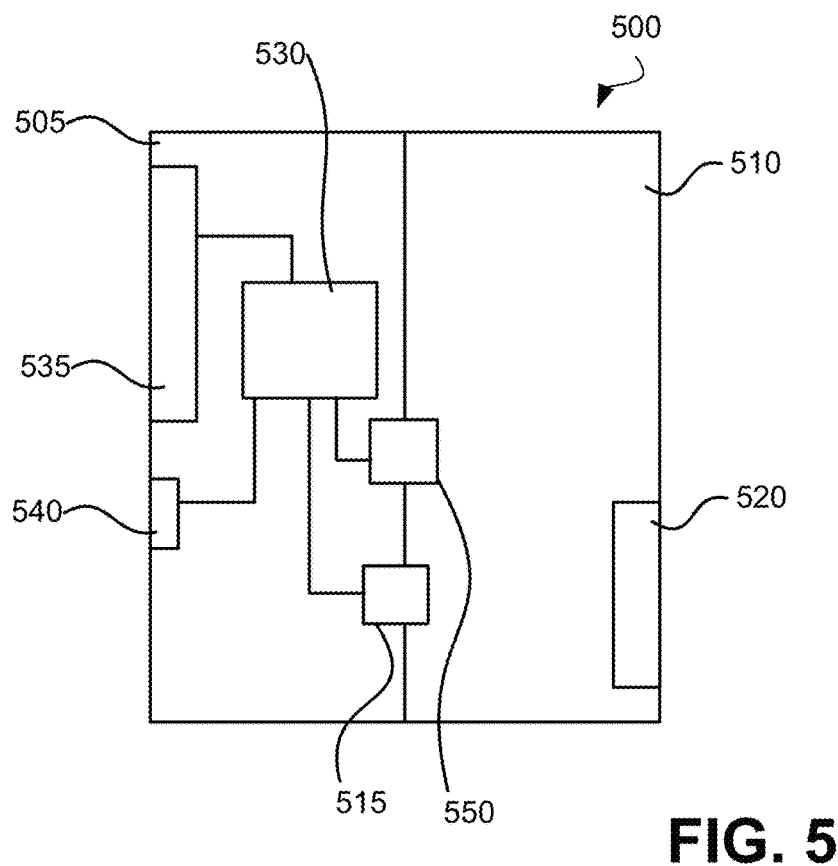
FIG. 5 illustrates an exemplary implementation of an aquatic environment water parameter testing system having an exemplary water agitation element.

FIG. 5 illustrates an exemplary implementation of an aquatic environment water parameter testing system 500. As with systems 300 and 400, testing system 500 is shown as a cross section of a three dimensional structure. Testing system 500 includes an electronics portion 505 and a sample chamber portion 510. Electronics portion 505 includes an optical reader element 515 aligned with a chemical indicator element 520 of sample chamber portion 510. Sample chamber portion 510 includes an opening (not shown). Electronics portion 505 includes, a processor 530, and a user interface including a display element 535 and a user input/output element 540. Electronics portion 505 includes one or more water agitation elements 550. An aquatic environment water parameter testing system may include one or more water agitation elements and associated circuitry and components for allowing a processor (such as processor element 530) to control the one or more water agitation elements. A water agitation element is configured to provide agitation to a water sample in a sample chamber of a sample chamber portion of an aquatic environment water parameter testing system. Agitation of a water sample may provide one or more benefits. Example benefits include, but are not limited to, moving water such that enhanced interaction between a constituent of the water and one or more chemical indicators, provide movement to materials in a water sample to help prevent settling of such materials on an optical reader element and or a chemical indicator, faster response, and any combinations thereof. Example components for a water agitation element include, but are not limited to, a spin wheel configured to be in contact with a water sample, a propeller configured to be in contact with a water sample, a moveable blade configured to be in contact with a water, a motor element to drive movement of a component of a water agitation element, ultrasonic transducer, and any combinations thereof. A component of a water agitation element may project outwardly from a surface of an electronics portion into a sample chamber. Water agitation element 550 is shown projecting outward and being connected to processor 530 for allowing processor 530 to control water agitation element 550.

Figure 6:
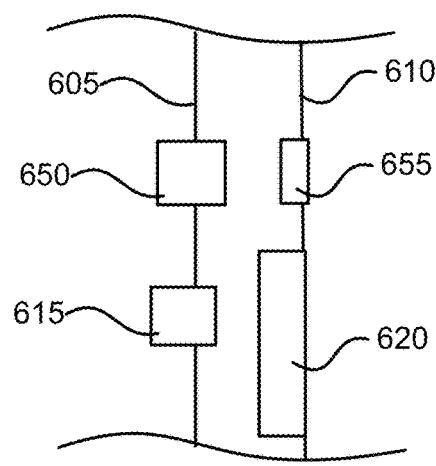
FIG. 6 illustrates an alternative implementation of a water agitation element.

FIG. 6 illustrates an alternative implementation of a water agitation element. FIG. 6 shows a cutaway cross sectional view of a wall 605 of an electronics portion opposite of a wall 610 of a sample chamber portion. An optical reader element 615 is shown aligned with a chemical indicator element 620. A first part 650 of a water agitation element is shown as extending from wall 605. In other examples, first part 650 may be more flush with wall 605, embedded behind wall 605, or placed in another configuration. A second part 655 of a water agitation element is shown as extending from wall 610. In other examples, second part 655 may be more flush with wall 610, embedded behind wall 610, or placed in another configuration. In one example first part 650 is an electromagnet and second part 655 is a permanent magnet. In such an example, first part 650 as an electromagnet can be pulsed to cause second part 655 to move in relation to first part 650 such as to cause wall 610 to move (even if slightly, e.g., with wall 610 made of a partially deformable material)

with respect to a water sample in the sample chamber. Such movement in such an example will cause agitation of the water sample.

Figure 7:
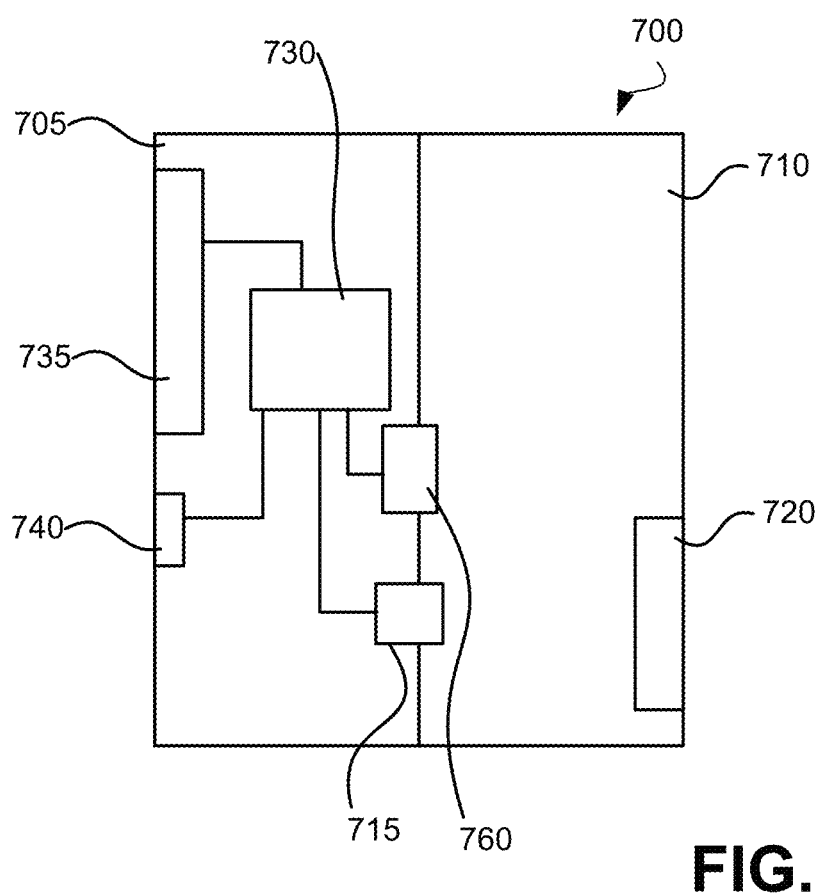
FIG. 7 illustrates an exemplary implementation of an aquatic environment water parameter testing system having an exemplary temperature measurement element.

FIG. 7 illustrates an exemplary implementation of an aquatic environment water parameter testing system 700. Testing system 700 is shown as a cross section of a three dimensional structure. Testing system 700 includes an electronics portion 705 and a sample chamber portion 710. Electronics portion 705 includes an optical reader element 715 aligned with a chemical indicator element 720 of sample chamber portion 710. Sample chamber portion 710 includes an opening (not shown). Electronics portion 705 includes, a processor 730, and a user interface including a display element 735 and a user input/output element 740. Electronics portion 705 includes one or more sample temperature measurement elements 760. An aquatic environment water parameter testing system may include one or more sample temperature measurement elements and associated circuitry and components for allowing a processor (such as processor element 530) to control the one or more sample temperature measurement elements. A sample temperature measurement element 760 includes a temperature conductive element that can be configured to be in contact with a water sample that is placed in the sample chamber of sample chamber portion 710. Sample temperature measurement element 760 also includes a temperature sensor connected to the temperature conductive element for determining a temperature value and/or data for determining a temperature value (e.g., using processor element 730). A sample temperature value may be used, for example, to correct for errors in one or more measured values (e.g., salinity, conductivity), to correct for errors in data values detected from one or more chemical indicators, and for any combination thereof. An example of using a sample temperature value for correcting conductivity is discussed below with respect to the method of FIG. 28. One alternative example implementation of a sample temperature measurement element includes using one or more of a conductivity electrode as temperature conductive element and connecting a temperature sensor to the conductivity electrode to determine a temperature of a water sample.

Figure 14:
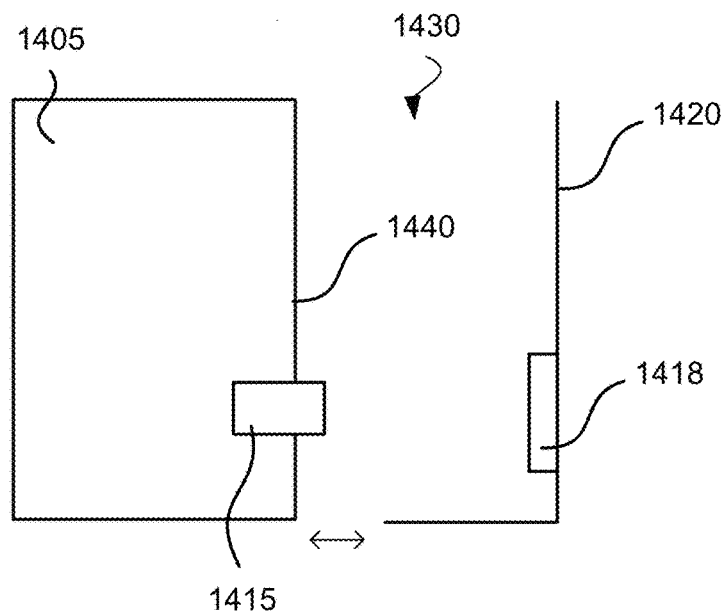
FIG. 14 illustrates an exemplary implementation a removable chemical indicator element with an exemplary aquatic environment water parameter testing system.

FIGS. 14 to 18, and 34 illustrate various configurations of an aquatic environment water parameter testing system showing different implementations of a removable chemical indicator element. Each example may have any one or more of the components discussed in this disclosure whether or not expressly shown in the examples. These examples are to show variations on removability of a chemical indicator element. FIG. 14 illustrates one example of an aquatic environment water parameter testing system having an electronics portion 1405. Electronics portion 1405 is shown with an optical reader element 1415 configured to align with one or more chemical indicators 1418 of a chemical indicator element 1420. In this example, chemical indicator element 1420 forms a substantial portion of the outer structural elements of a sample chamber portion with an opening 1430 for providing a water sample to a sample chamber that is formed by chemical indicator element 1420 and an outer surface 1440 of electronics portion 1405 when chemical indicator element 1420 is securely connected to electronics portion 1405. Chemical indicator element 1420 is shown disconnected from electronics portion 1405. An attachment element and/or a water sealing element (not shown) can be used to securely connect chemical indicator element 1420. Chemical indicator element 1420 is shown disconnected from electronics portion 1405. In one example, when chemical indicator element 1420 is connected the aquatic environment water parameter testing system appears to be an integral system with a cohesive outer housing. A cover may be included to close opening 1430.

Figure 15:
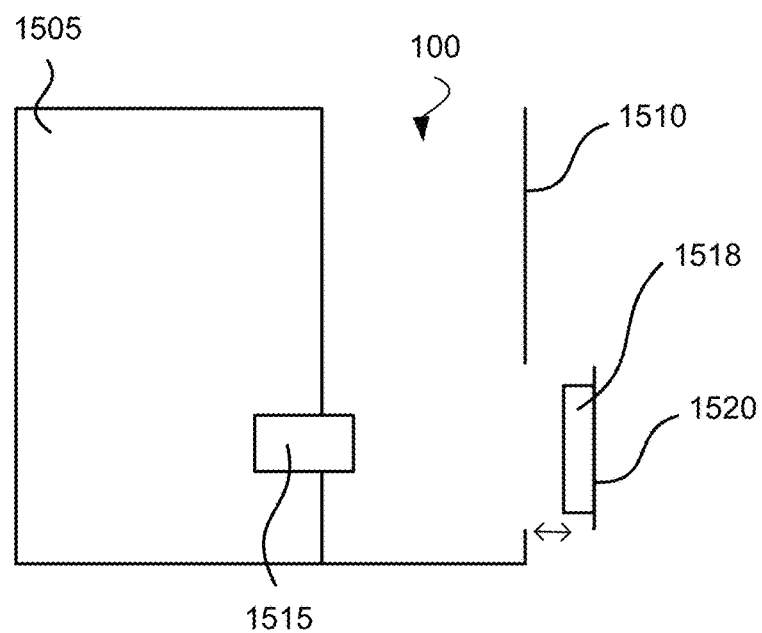
FIG. 15 illustrates another exemplary implementation a removable chemical indicator element with an exemplary aquatic environment water parameter testing system.

FIG. 15 illustrates another example of an aquatic environment water parameter testing system having an electronics portion 1505 and a sample chamber portion 1510. Electronics portion 1505 is shown with an optical reader element 1515 configured to align with one or more chemical indicators 1518 of a chemical indicator element 1520. In this example, sample chamber portion 1510 includes an opening 1530 for providing a water sample to a sample chamber that is formed by one or more structural wall portions of sample chamber portion 1510 and chemical indicator element 1520 when chemical indicator element 1520 is connected to a second opening in sample chamber portion 1510 closing the opening. An attachment element and/or a water sealing element (not shown) can be used to securely connect chemical indicator element 1520. Chemical indicator element 1520 is shown disconnected from sample chamber portion 1510. In one example, when chemical indicator element 1520 is connected the aquatic environment water parameter testing system appears to be an integral system with a cohesive outer housing. In one exemplary aspect, when chemical indicator element 1520 is connected it forms a part of sample chamber portion 1510. A cover may be included to close opening 1530.

Figure 16:
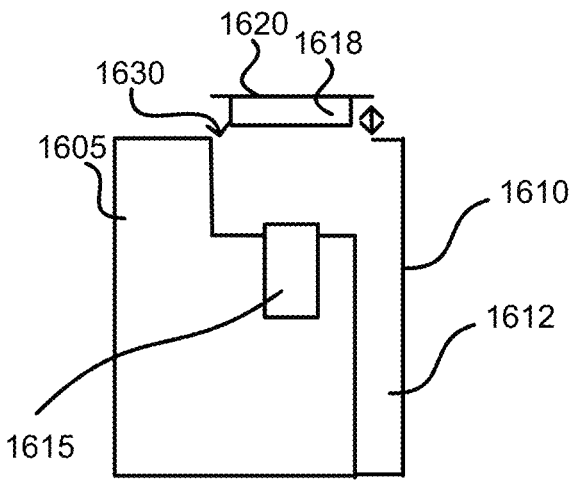
FIG. 16 illustrates yet another exemplary implementation a removable chemical indicator element with an exemplary aquatic environment water parameter testing system.

FIG. 16 illustrates another example of an aquatic environment water parameter testing system having an electronics portion 1605 and a sample chamber portion 1610 forming a sample chamber 1612 between one or more walls of sample chamber portion 1610 and a plurality of outer surfaces of electronics portion 1605. Electronics portion 1605 is shown with an optical reader element 1615 configured to align with one or more chemical indicators 1618 of a chemical indicator element 1620. In this example, sample chamber portion 1610 includes an opening 1630 for providing a water sample to sample chamber 1612. Chemical indicator element 1620 acts also as a cover for opening 1630. An attachment element and/or a water sealing element (not shown) can be used to securely connect chemical indicator element 1620. Chemical indicator element 1620 is shown disconnected from sample chamber portion 1610. In one example, when chemical indicator element 1620 is connected the aquatic environment water parameter testing system appears to be an integral system with a cohesive outer housing. In one exemplary aspect, when chemical indicator element 1620 is connected it forms a part of sample chamber portion 1610. In one example of use, a water sample is placed in sample chamber 1612, chemical indicator element 1620 is securely connected to close opening 1630, the aquatic environment water parameter testing system is inverted to allow air to move away from chemical indicator 1618 and to allow chemical indicator 1618 to be fully in contact with the water sample (with water sample also in contact with optical reader element 1615.

Figure 34:
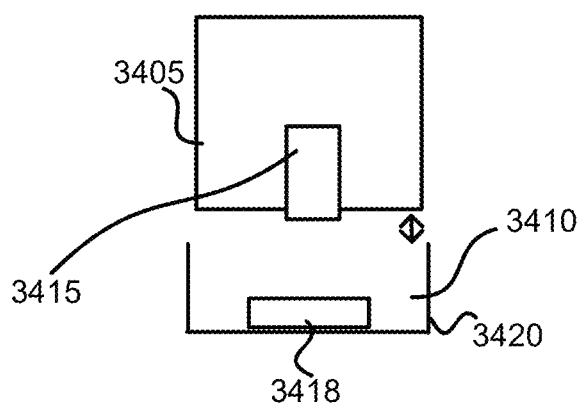
FIG. 34 illustrates a further exemplary implementation a removable chemical indicator element with an exemplary aquatic environment water parameter testing system.

FIG. 34 illustrates another example of an aquatic environment water parameter testing system having an electronics portion 3405 and a sample chamber portion 3410. Optical reader 3415 is shown directed downwardly directed to a chemical indicator 3418 as part of a chemical indicator element 3420. In the example shown, chemical indicator element 3420 forms sample chamber portion 3410. In other examples, chemical indicator element 3420 may take a different form, such as being removable from sample chamber portion 3410 (e.g., adhesively attached to a surface of sample chamber portion 3410, removably connected as in one of the other examples disclosed herein, etc.). Electronic portion 3405 is shown separated from sample chamber portion 3410. Arrows indicate connectability of electronic portion 3405 with sample chamber portion 3410. Connectivity may be by a variety of ways including, but not limited to, insertion of electronic portion 3405 partially within sample chamber portion 3410, snap connection, other connections described with respect to other examples herein, screw connection, and/or other connection. In one example of use, a water sample may be placed in sample chamber portion 3410 and made to come into contact with chemical indicator 3418 (e.g. for a period of time sufficient to cause chemical indicator 3418 to undergo a detectable change). A user may then connect electronic portion 3405 to sample chamber portion 3410 such to bring optical reader 3415 in alignment with chemical indicator 3418 (e.g., making contact between optical reader 3415 and the water sample). As with other examples of this disclosure chemical indicator element 3420 may be swappable to allow for cleaning and/or use of different chemical indicators configured to test for different components in a water sample.

Figure 17:
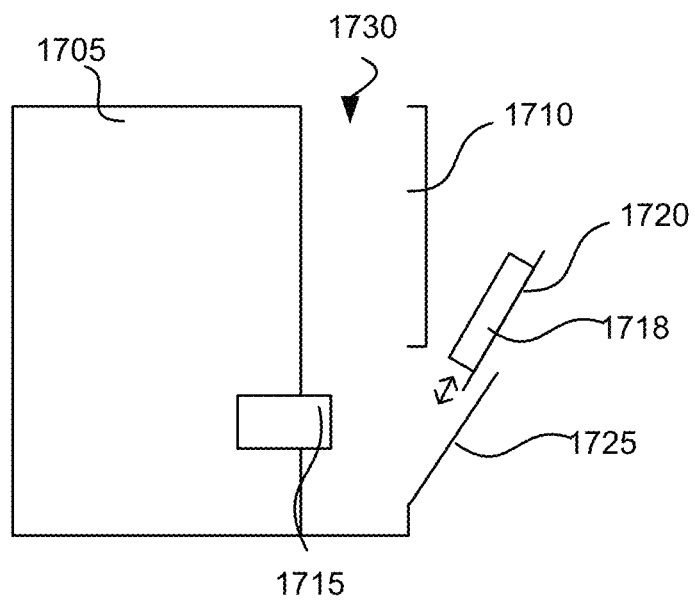
FIG. 17 illustrates still another exemplary implementation a removable chemical indicator element with an exemplary aquatic environment water parameter testing system.

FIG. 17 illustrates another example of an aquatic environment water parameter testing system having an electronics portion 1705 and a sample chamber portion 1710. Electronics portion 1705 is shown with an optical reader element 1715 configured to align with one or more chemical indicators 1718 of a chemical indicator element 1720 when chemical indicator element 1720 is inserted/attached to a door element 1725 that is configured to close over a second opening in sample chamber portion 1710. In this example, sample chamber portion 1710 includes an opening 1730 for providing a water sample to a sample chamber that is formed by one or more structural wall portions of sample chamber portion 1710 and chemical indicator element 1720 and door 1725 when chemical indicator element 1720 is connected to door 1725 and door 1726 is closed upon second opening in sample chamber portion 1710 closing the opening. An attachment element and/or a water sealing element (not shown) can be used to securely close door 1725 and connect chemical indicator element 1720 to door 1725. Chemical indicator element 1720 is shown disconnected from sample chamber portion 1710. In one example, when chemical indicator element 1720 is connected and door 1725 is closed, the aquatic environment water parameter testing system appears to be an integral system with a cohesive outer housing. In one exemplary aspect, when chemical indicator element 1720 is connected it forms a part of sample chamber portion 1710. A cover may be included to close opening 1730.

Figure 18:
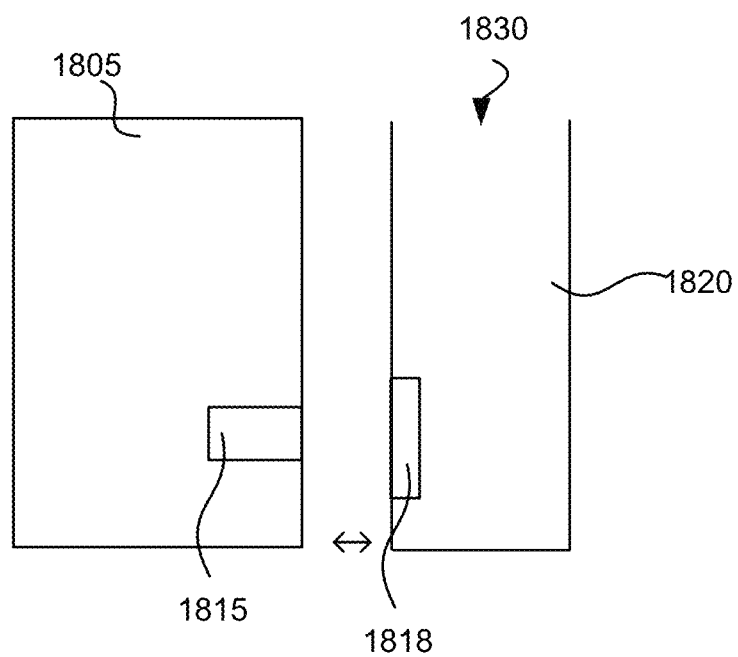
FIG. 18 illustrates yet still another exemplary implementation a removable chemical indicator element with an exemplary aquatic environment water parameter testing system.

FIG. 18 illustrates another example of an aquatic environment water parameter testing system having an electronics portion 1805. Electronics portion 1805 is shown with an optical reader element 1815 configured to align with one or more chemical indicators 1820 of a chemical indicator element 1820 that forms a sample chamber with an opening 1830 for providing a water sample to the sample chamber. An attachment element (not shown) can be used to connect chemical indicator element 1820 to electronics portion 1805. In this example, chemical indicator element 1820 includes a portion that is transparent to one or more wavelengths of light and aligns with optical reader element 1815 and chemical indicator 1818 to allow light for illumination and for reading to pass between the two components when chemical indicator element 1820 is connected. Chemical indicator element may include a backing material and a holder material as part of the structure of chemical indicator element 1820 similar to the configuration of FIG. 12. In one example, the aquatic environment water parameter testing system appears to be an integral system with a cohesive outer housing. A cover may be included to close opening 1830.

Figure 19:
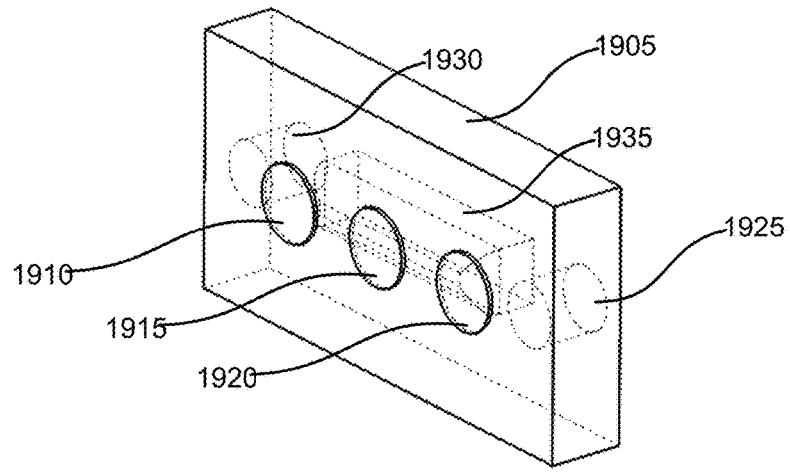
FIG. 19 illustrates an example of a chemical indicator element.

FIG. 19 illustrates an example of a chemical indicator element 1905 having chemical indicators 1910, 1915, 1920 arranged on a first face and attachment elements 1925 and 1930 on an opposite face. In one example attachment elements 1925 and 1930 are magnetic elements that can mate with one or more magnetic elements of a sample chamber portion. In one such example, chemical indicator element 1905 attaches to a door element, such as door element 1725 of FIG. 17. Chemical indicator element 1905 also includes an RFID element 1935. In an alternative configuration RFID element 1935 is displaced above or below the array of chemical indicators 1910, 1915, 1920 to allow for mating with an RFID reader of an electronics portion.

Figure 20:
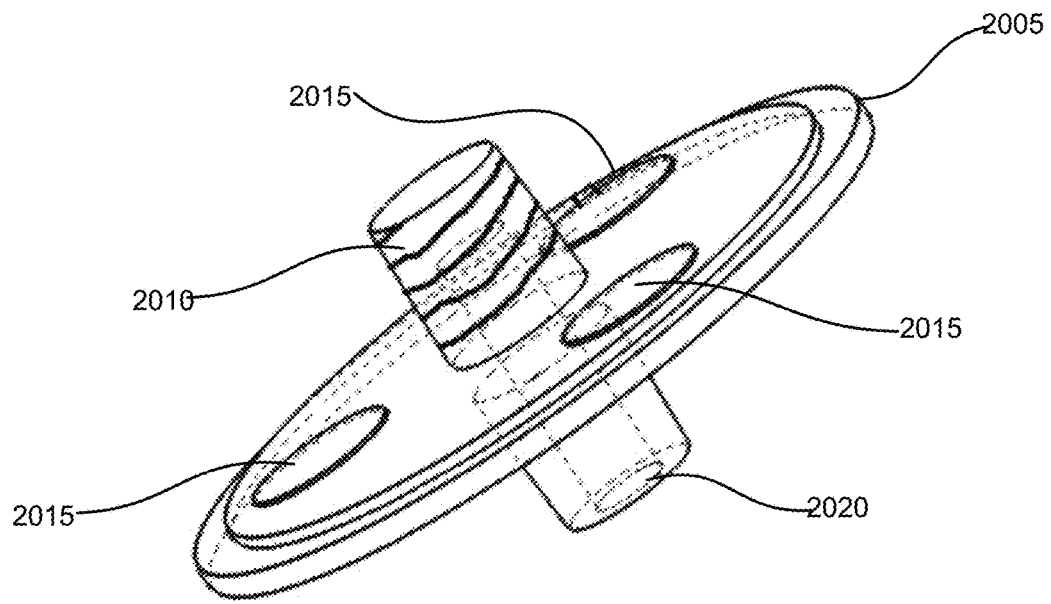
FIG. 20 illustrates another example of a chemical indicator element.

FIG. 20 illustrates another example of a chemical indicator element 2005 having a circular configuration with a threaded attachment element 2010 and an array of chemical indicators 2015 and an RFID tag hole 2020 opposite the threaded attachment. RFID tag hole 2020 may include an RFID element or other information storage and communication element. In an example of use, the chemical indicator element 2005 may be connected to a sample chamber portion using a mating of the threading element 2010 with another threaded element of the sample chamber portion (e.g., as a cover to a water sample opening or another opening in a sidewall of the sample chamber portion. In another implementation, the chemical indicator element 2005 includes an alignment assistance mark to allow for alignment of chemical indicators with corresponding optical reader elements.

Figure 21:
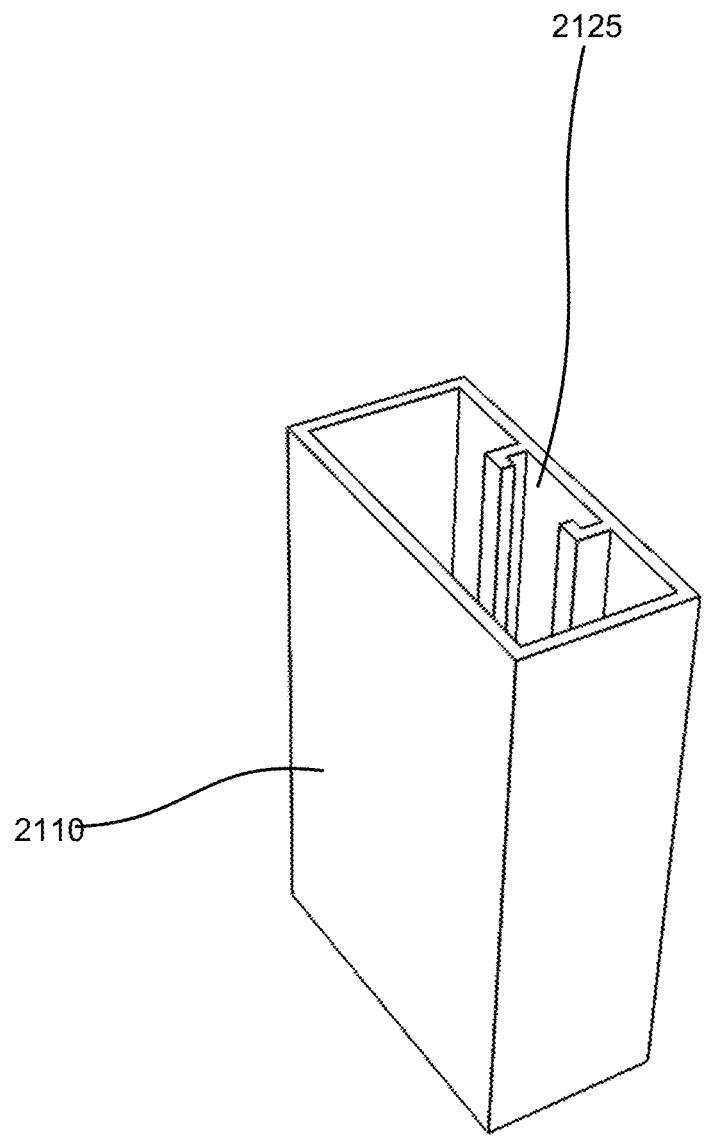
FIG. 21 illustrates an example of a sample chamber portion having an exemplary slot attachment element.

FIG. 21 illustrates an example of a sample chamber portion 2110 having a slot attachment element 2125 for receiving a chemical indicator element configured to mate with slot attachment element 2125. Sample chamber portion 2110 may be associated with an electronics portion in any of the ways that are disclosed in the current disclosure of interrelationships between sample chamber portions and electronics portions. In one example, a chemical indicator element can slide into the mating features of slot attachment element 2125 by way of user insertion. When a chemical indicator element is to be replaced with a new chemical indicator element or new type of chemical indicator element, a user can slide the element up and out of contact with the chamber portion. The slot can have end-stops to provide an alignment limiter at the bottom of the chamber or at any height above the bottom such that the chemical indicator element comes into alignment with the one or more electro-optical reader element(s).

FIGS. 22 and 23 illustrate examples of user interfaces on an outer portion of an electronics portion of an aquatic environment water parameter testing system. FIG. 22 shows an electronics portion 2205 having a display element 2210 and user input/output elements 2215, 2220, and 2225. FIG. 23 shows an electronics portion 2305 having a display element 2310 and user input/output elements 2315, 2320, and 2325. FIG. 24 shows an exemplary surface of an electronics portion 2405 that in use comes into contact with a sample chamber. The surface of electronics portion 2405 shows exposed portions of three optical reader elements 2410, 2415, 2420 and two conductivity electrodes 2425 and 2430.

Figure 25A:
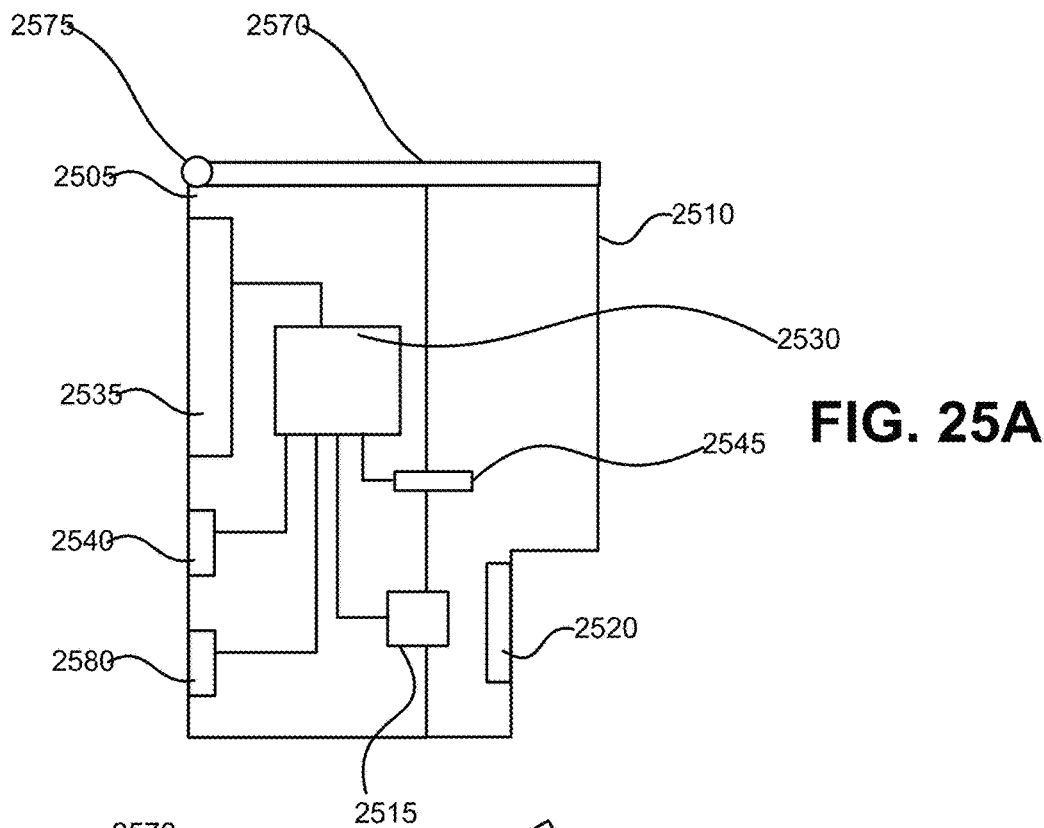
FIG. 25A illustrates a first view of one exemplary implementation of an aquatic environment water parameter testing system having an exemplary cover with a hinged attachment.
Figure 25B:
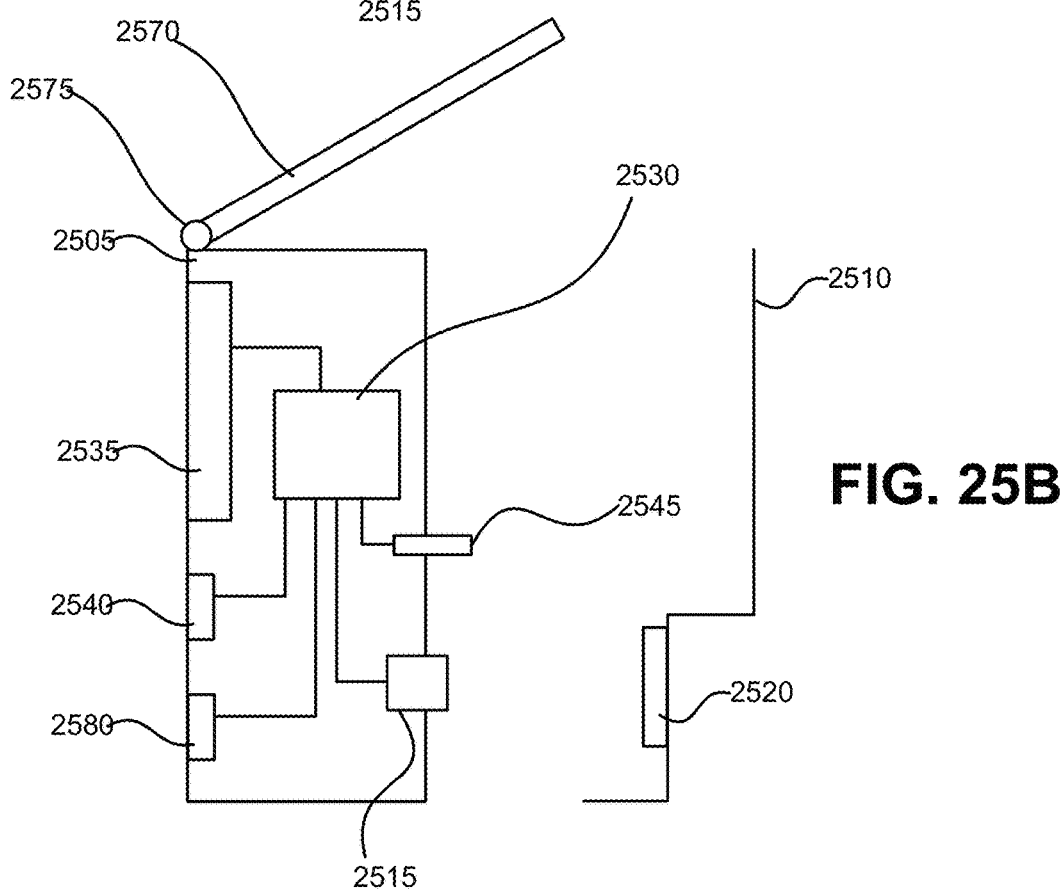
FIG. 25B illustrates a second view of the exemplary implementation of an aquatic environment water parameter testing system having an exemplary cover with a hinged attachment.

FIGS. 25A, 25B, 26A, and 26B illustrate exemplary implementation having a hinged cover that covers an opening in a sample chamber. Components have similar features as corresponding components discussed above with other examples. FIGS. 25A and B illustrate one exemplary implementation of an aquatic environment water parameter testing system having an electronics portion 2505 and a sample chamber portion 2510, an optical reader element 2515, a chemical indicator element 2520, a processor element 2530, a display element 2535, user input/output elements 2540, 2580, and a conductivity element 2545. The aquatic environment water parameter testing system also includes a cover 2570 with a hinged attachment 2575 for opening and closing cover 2570 over an opening of a sample chamber formed when sample chamber portion/chemical indicator element 2510/2520 is connected to electronics portion 2505. FIG. 25B shows cover 2570 open and sample chamber portion/chemical indicator element 2510/2520 disconnected. In this example, sample chamber portion/chemical indicator element 2510/2520 has a configuration that brings chemical indicators closer to optical element 2515 while having a larger portion of sample chamber above.

Figures 26A, 26B:
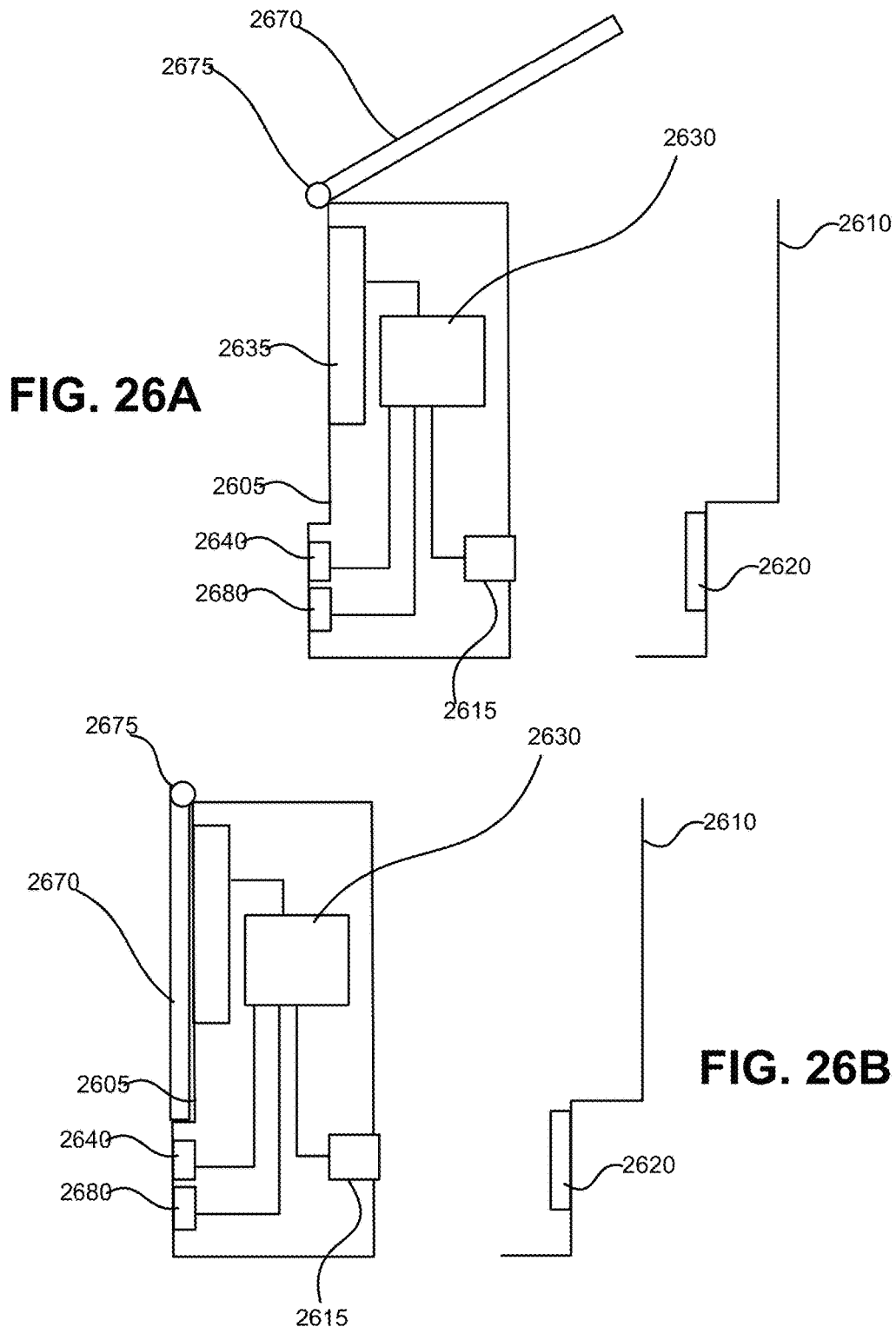
FIG. 26A illustrates a first view of another exemplary implementation of an aquatic environment water parameter testing system having another exemplary cover with a hinged attachment.
FIG. 26B illustrates a second view of the exemplary implementation of an aquatic environment water parameter testing system having another exemplary cover with a hinged attachment.

FIGS. 26A and B illustrate one exemplary implementation of an aquatic environment water parameter testing system having an electronics portion 2605 and a sample chamber portion 2610, an optical reader element 2615, a chemical indicator element 2620, a processor element 2630, a display element 2635, user input/output elements 2640, 2680, and a conductivity element 2645. The aquatic environment water parameter testing system also includes a cover 2670 with a hinged attachment 2675 for opening and closing cover 2670 over an opening of a sample chamber formed when sample chamber portion/chemical indicator element 2610/2620 is connected to electronics portion 2605. FIG. 26B shows cover 2670 open and sample chamber portion/chemical indicator element 2610/2620 disconnected. In this example, electronics portion 2605 is configured to allow cover 2670 to swing around when not covering opening in sample chamber to cover display 2635 and/or stow cover 2670 when sample chamber portion/chemical indicator element 2610/2620 is disconnected.

Figure 27:
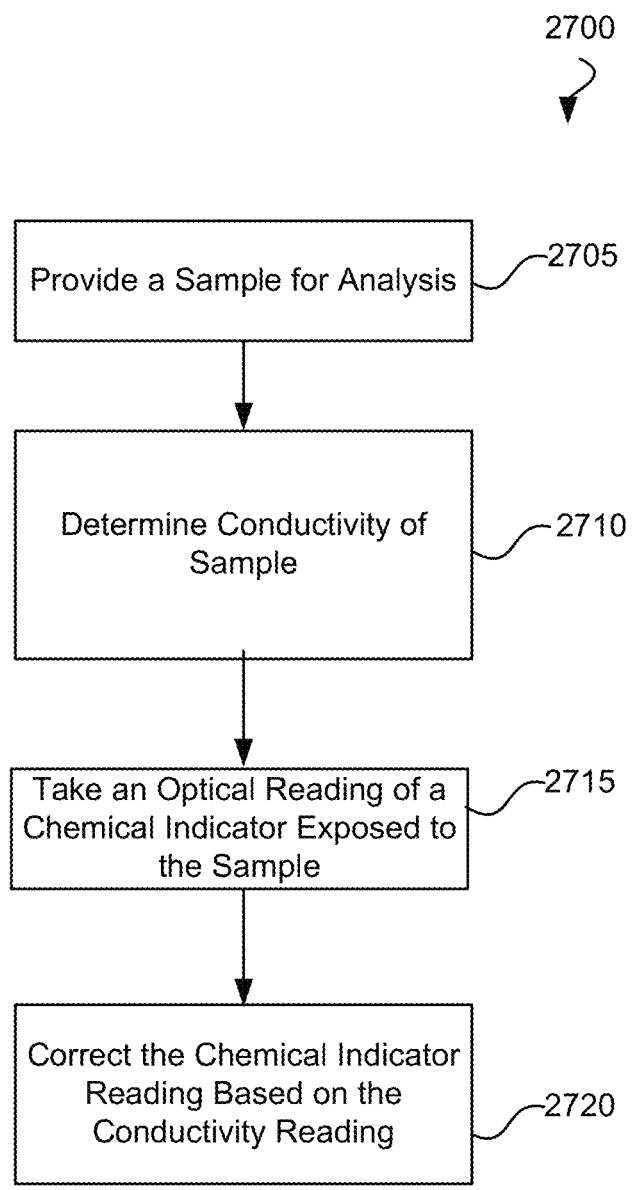
FIG. 27 illustrates an example of a method for calibrating a data reading from an optical reader element from a chemical indicator.

FIG. 27 illustrates an example of a method 2700 for calibrating a data reading from an optical reader element from a chemical indicator in which an optical reading (e.g., information of a physical change of a chemical indicator exposed to a sample as measured from an optical sensor of the optical reader element) is corrected based on the conductivity of the sample. At step 2705, a sample is provided for analysis (e.g., a liquid sample is placed in a sample chamber of an aquatic environment water parameter testing system of the current disclosure). At step 2710, a conductivity value for the sample is determined (e.g., using a conductivity measurement element, such as conductivity element 445 of FIG. 4). At step 2715, an optical reading of a chemical indicator that is exposed to the sample is taken (e.g., using an optical reader of an aquatic environment water parameter testing system of the current disclosure a reading including information of a physical change of the chemical indicator is taken). At step 2720, the optical reading is corrected using the conductivity value. An optical reading may fluctuate based on the conductivity of the sample. The correction done in step 2720 attempts to account for this fluctuation. Such a correction may be done in a variety of ways. In one example, known data curves for optical readings corresponding to certain known amounts of a constituent (e.g., pH, calcium concentration, etc.) of a sample at specific conductivities can be recorded and stored (e.g., in a memory of the aquatic environment water parameter testing system). In one such example, using data curves for values at two conductivities (e.g., an example conductivity of a salt water sample and an example conductivity of a fresh water sample), values for a constituent at other conductivities that are measured for a given sample can be calculated with reference to the known data curves. Examples of this are shown below with respect to FIGS. 29A and 29B.

Conductivity readings may fluctuate themselves based on the temperature of a given sample. Correction of a measured conductivity reading may be calibrated based on the temperature of the sample. For example, known temperature coefficients (e.g., well known temperature to conductivity relationships for given sample types and/or temperature to conductivity relationships measured for a particular sample type, such as at the manufacturing of an aquatic environment water parameter testing system) can be utilized. In one example, these values can be stored in a memory of an aquatic environment water parameter testing system according to the current disclosure. A temperature coefficient can then be used (e.g., by a processing element) to calibrate a measured conductivity value to a particular temperature (also measured, such as with a temperature measurement element of an electronics portion of an aquatic environment water parameter testing system). In some examples, a cell constant for the device used to measure the conductivity can also be used to normalize a conductivity reading. Cell constants and how to use them in normalization are understood by those of ordinary skill. If normalization is not desired, the use of cell constants in the correction can be omitted. Additionally, as discussed above, a temperature of an optical reader element may be utilized to correct an optical reading for fluctuations due to the temperature of a component of the optical reader element.

Figure 28:
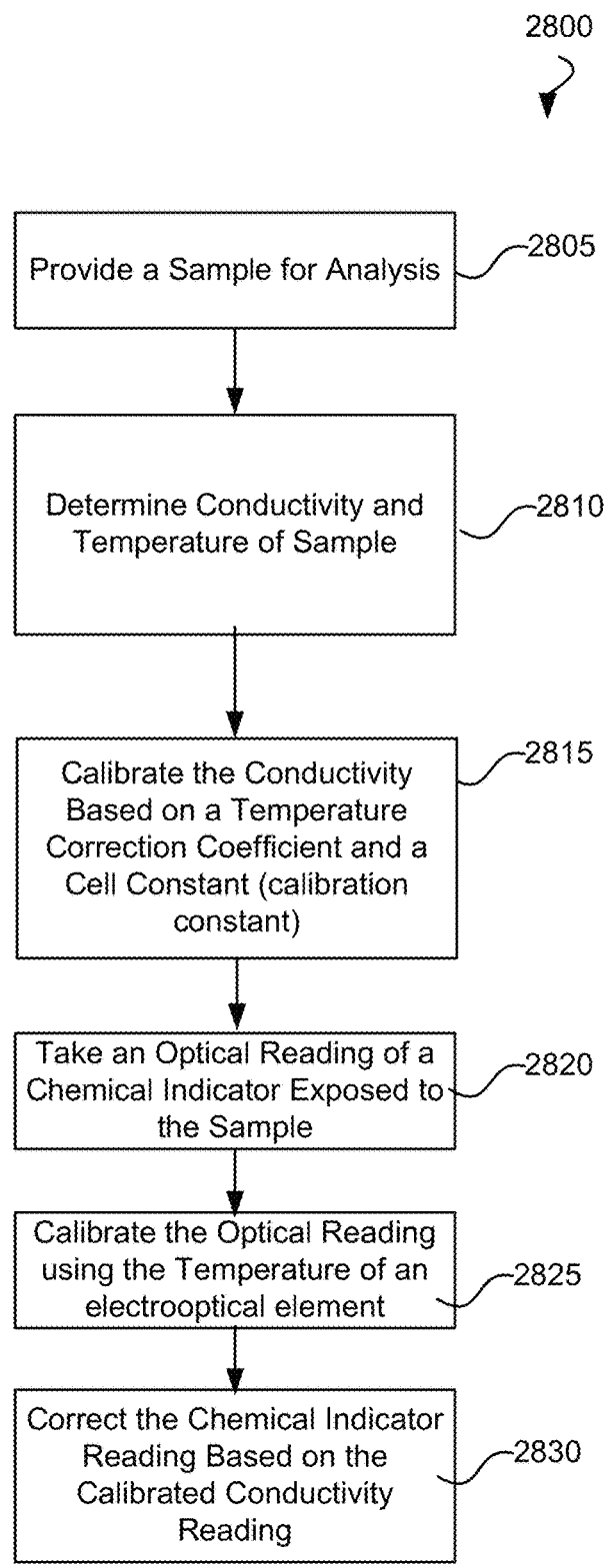
FIG. 28 illustrates an example of a method for calibrating a data reading from an optical reader element for the temperature of a component of the optical reader element and for the conductivity of the sample

FIG. 28 illustrates an example of a method 2800 for calibrating a data reading from an optical reader element for the temperature of a component of the optical reader element and for the conductivity of the sample. In this example, the conductivity of the sample is also corrected for the temperature of the sample. It is noted that either the corrections for the temperature can be omitted from the method. At step 2805, a sample is provided for analysis (e.g., via placement in a sample chamber of an aquatic environment water parameter testing system of the current disclosure). At step 2810, a conductivity measurement is made of the sample and a temperature measurement is made of the sample (e.g., using a temperature measurement element and a conductivity measurement element of an aquatic environment water parameter testing system of the current disclosure). At step 2815, a calibration is made of the conductivity to correct for temperature variation in conductivity. For example, a temperature correction coefficient and a cell constant can be utilized to adjust the conductivity based on the temperature of the sample. In one such example, an aquatic environment water parameter testing system may include a calibration table (e.g., stored in memory) having information for conductivity values versus temperature values that have been measured previously (e.g., at manufacture) based on a standard conductivity sample. At step 2820, an optical reading of a chemical indicator that is exposed to the sample is taken (e.g., using an optical reader of an aquatic environment water parameter testing system of the current disclosure). At step 2825, the optical reading is calibrated using a temperature of an electrooptical element (e.g., one or more components of an optical reader) used to take the optical reading. In one example, such a temperature is taken by using a temperature measurement circuit/device in proximity to the one or more components of an optical reader. Calibration may be made based on a known (e.g., measured at time of manufacture or previously) temperature dependence of a chemical indicator measurement made by the electrooptical element (e.g., due to LED light source intensity changes due to temperature changes in the LED light, causing differing amounts of light incident on a chemical indicator). At step 2830, the temperature corrected optical reading of the chemical indicator is then corrected using the calibrated conductivity measurement from step 2815.

Figure 29A:
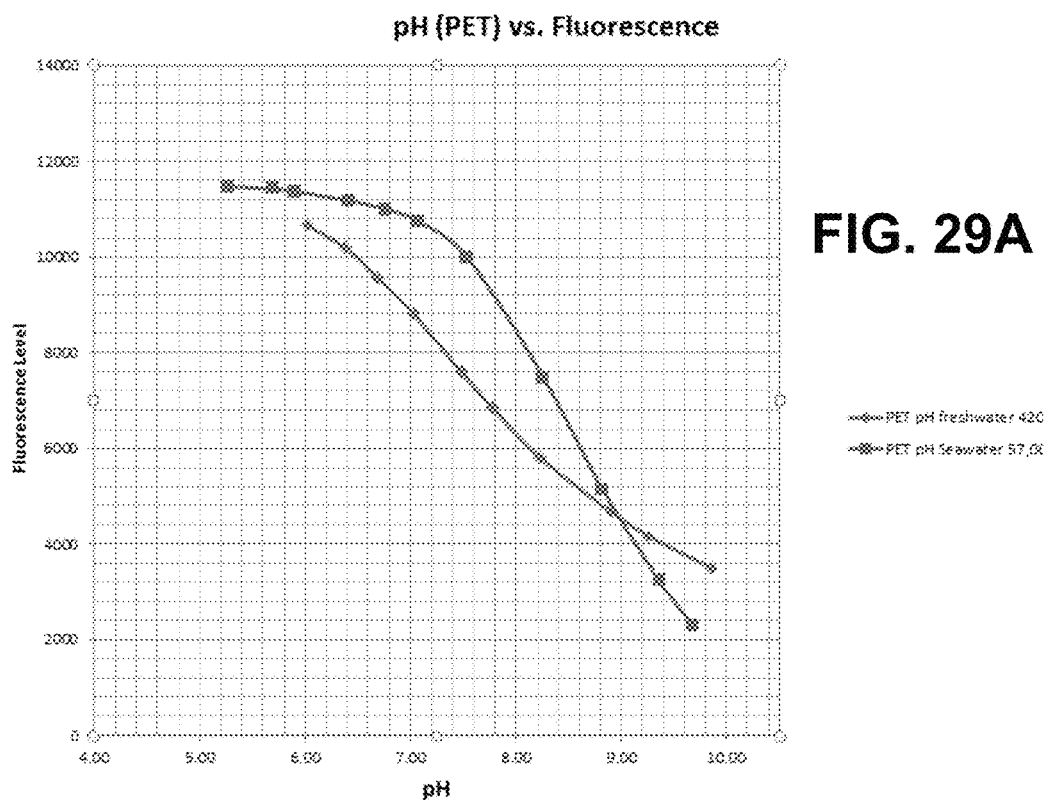
FIG. 29A illustrates a plot of exemplary response curves for a given constituent level of an example sample correlated to an optical light reading measured by an optical reading element

FIG. 29A illustrates a plot of exemplary response curves for a given constituent level of a sample (in this case pH) correlated to the optical light reading (in this case fluorescence light levels) measured by an optical reading element. The response data curves shown are derived from measured values of optical readings corresponding to known pH levels for two different samples at different conductivities. In this example, the two conductivities are at 57,000 micro Siemens conductivity (the data curve that starts at the left with higher values of fluorescence), which corresponds to an approximate seawater sample and at 420 micro Siemens conductivity (the data curve that starts at the left with lower values for fluorescence), which corresponds to an approximate fresh water sample. Values such as these can be used to determine a constituent level in a sample at a different conductivity. For example, the two data curves can be related to each other using formulas that relate the conductivity with respect to the desired constituent to determine the conductivity corrected value for the constituent at a given third conductivity value for the sample. One desired constituent, pH, is a log based scale. In one example, the following formula can be utilized to relate two known data curves for pH versus optical reading values at known conductivities:

$$pH_{corrected} = \frac{\log\left(\frac{\mu_X}{\mu_2}\right)}{\log\left(\frac{\mu_1}{\mu_2}\right)}(pH_{\mu_1} - pH_{\mu_2}) + pH_{\mu_2}$$

where $\mu_X$ is the conductivity measured for a given sample (e.g., using a conductivity measurement device), $\mu_1$ and $\mu_2$ are the conductivity values from for the two known data curves (such as those in FIG. 29A) wherein $\mu_1$ is the conductivity value of the higher conductivity curve and $\mu_2$ is the conductivity value of the lower conductivity curve, $pH_{\mu_1}$ is the pH on the $\mu_1$ curve at the measured fluorescence value (e.g., the pH at the optical reading measured at the optical reader element), $pH_{\mu_2}$ is the pH on the $\mu_2$ curve at the measured fluorescence value (e.g., the pH at the optical reading measured at the optical reader element), and $pH_{corrected}$ is the pH value that is corrected for conductivity for the particular optical reading. In another example, a non-log-based constituent may use non-log-based ratio equations, such as the one above without the log function to determine the interrelationship.

Figure 29B:
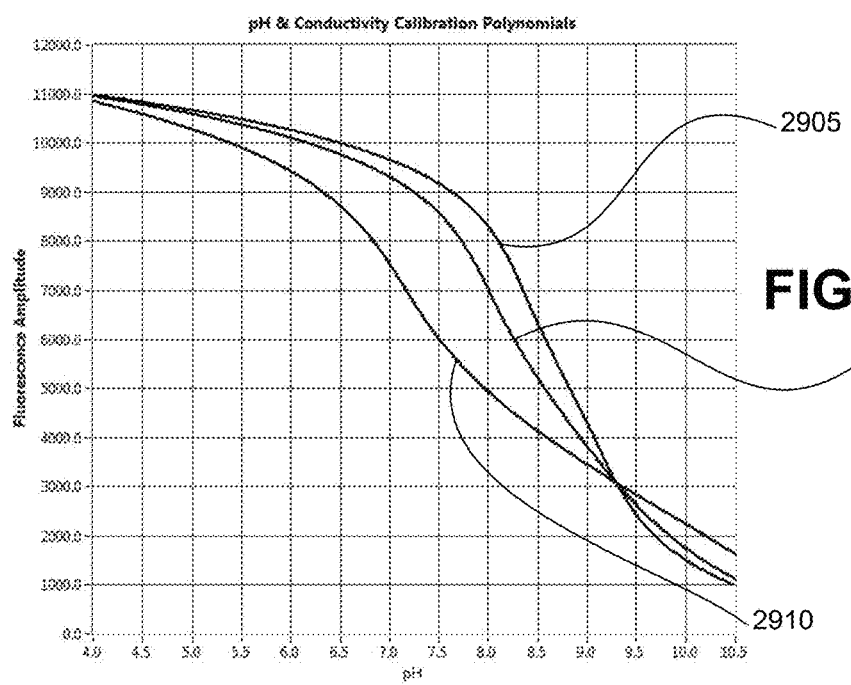
FIG. 29B illustrates another example of data curves plotted from known values at two particular conductivities and a calculated data curve.

FIG. 29B illustrates another example of data curves plotted from known values at two particular conductivities and a calculated data curve determined using an equation relationship such as the one for pH discussed in the previous example and the two known data curves. Data curve 2905 is a plot of optical reading values (in this case fluorescence) from an optical reader element corresponding to pH values for a sample at a given conductivity of 50,000 micro Siemens. Data curve 2910 is a plot of optical reading values (in this case fluorescence) from an optical reader element corresponding to pH values for a sample at a given conductivity of 500 micro Siemens. Data curves 2905 and 2910 can be measured for known samples and the data stored in a memory element accessible by a processing element of an aquatic environment water parameter testing system. Data curve 2915 is a plot of calculated optical reading values (in this case fluorescence) corresponding to pH values for a sample at a given conductivity of 18,000 micro Siemens. Data curve 2915, in this example, is calculated using the data of data curves 2905 and 2910 and the pH equation from the sample above.

Figure 30:
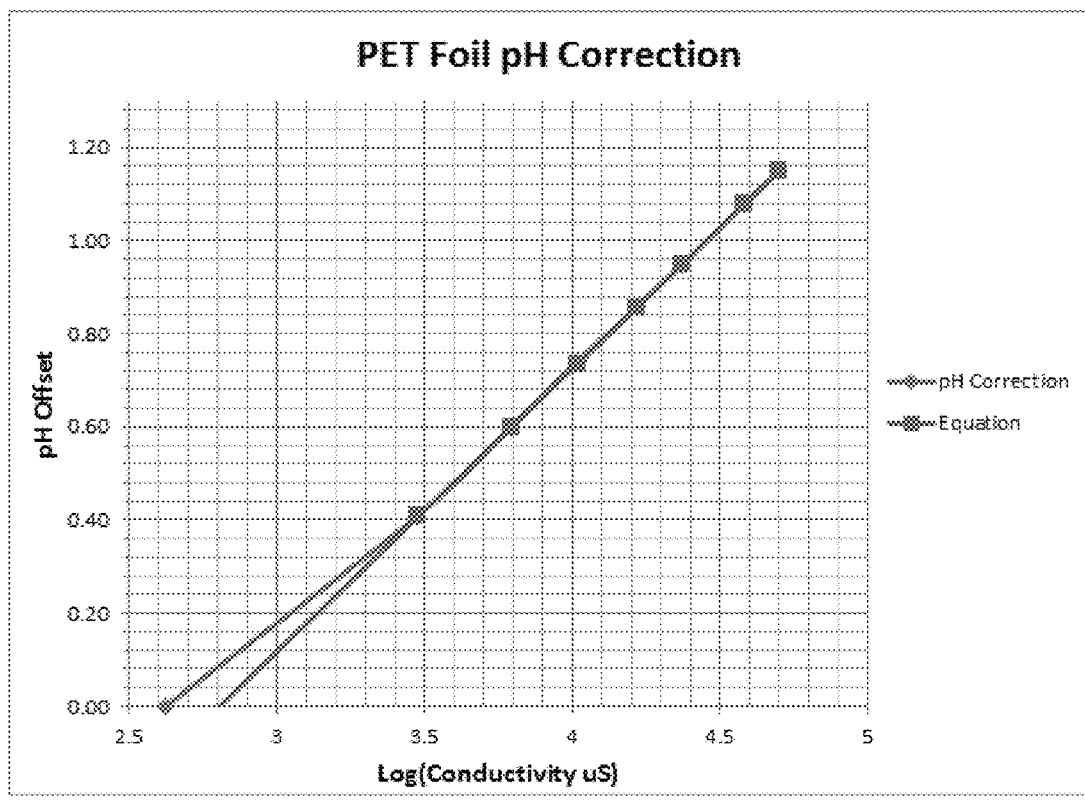
FIG. 30 illustrates an exemplary plot showing a sample correction in pH.

FIG. 30 illustrates an exemplary plot showing a correction in pH to be applied to for any conductivity for an example similar to the one discussed in FIGS. 29A and 29B.

Figure 36:
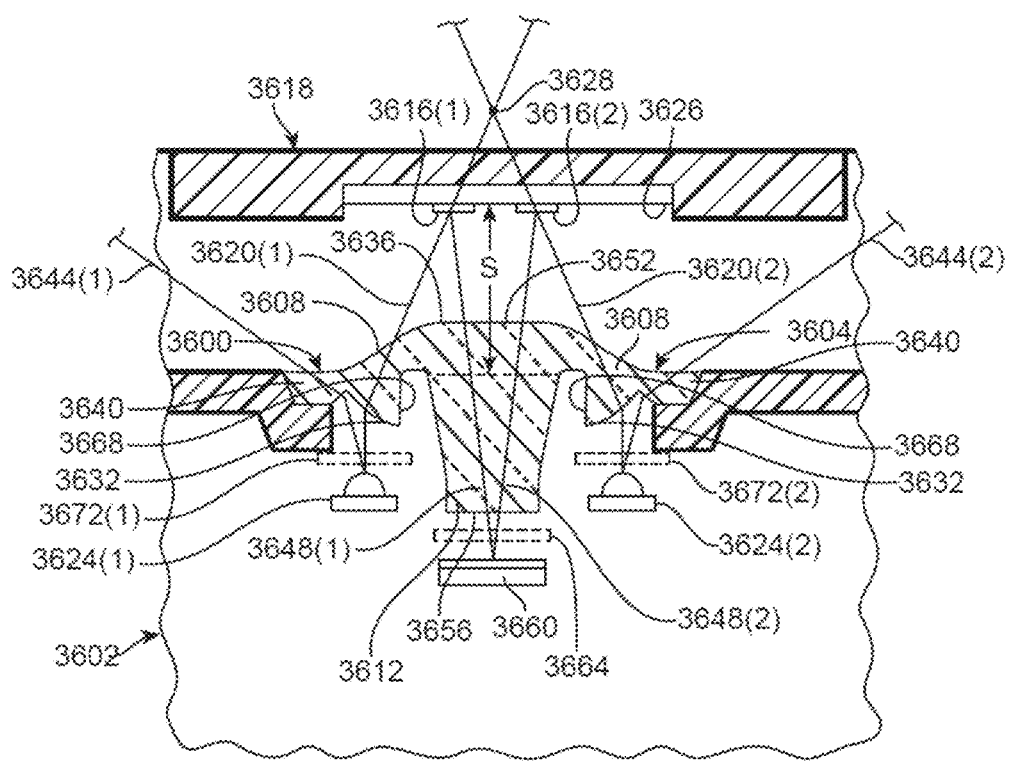
FIG. 36 illustrates an example of an optical reader element.
Figure 37:
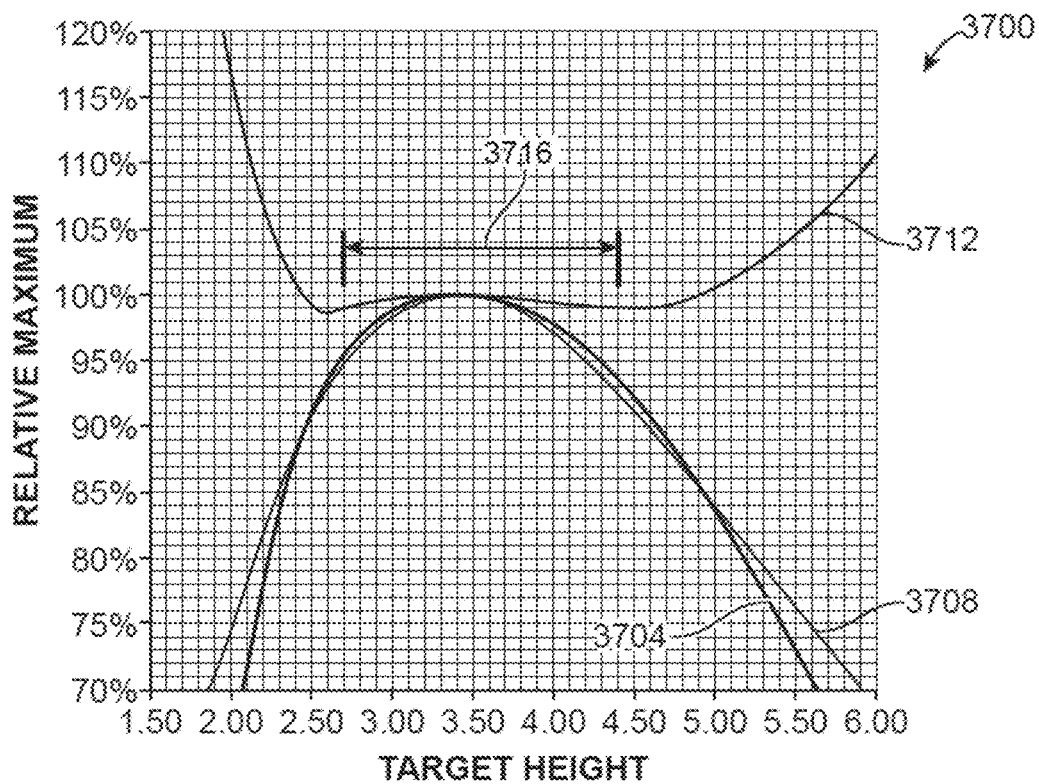
FIG. 37 illustrates an exemplary curve representing a detected intensity, as a percentage of maximum intensity, of an illumination spot formed by an example combined I/LC.

FIG. 36 illustrates an example of an optical reader element 3600 (which is referred to also in this discussion as a combined illuminator/light collector (I/LC) combined I/LC 3600) that can be used in an aquatic environment water parameter testing system according to the current disclosure or, for example, in any other suitable embodiment of a monitoring unit made in accordance with the present disclosure. As seen in FIG. 36, combined I/LC 3600 comprises a unitary monolithic body 3604 formed from one or more translucent materials, such as acrylic plastic, polycarbonate plastic, glass, sapphire, etc. In one example, when made of a moldable material, monolithic body 3604 can be molded, with little to no subsequent machining or other processing. Combined I/LC 3600 includes spot lensing 3608 and a light pipe 3612. Spot lensing 3608 is designed and configured to project individual spots of light, here, two spots 3616(1) and 3616(2) of light 3620(1) and 3620(2), onto chemical indicator disc 816 (i.e., the target), wherein each spot projected is based on light emitted from a corresponding light source, here, light sources 3624(1) and 3624(2), respectively. In a particular embodiment spot lensing similar to lensing 3608 can be used to project four spots of light onto the corresponding chemical indicator apparatus, two spots for reflectivity measurements and two spots for fluorescence or absorbance measurements.

In one implementation spot lensing 3608 is carefully designed and configured in conjunction with the spacing, S, between combined I/LC 3600 and the surface 3626 of disc 816 to provide highly precisely sized and located spots 3616(1) and 3616(2). As seen in FIG. 36, spot lensing 3608 is designed and configured so that light 3620(1) and 3620(2) passing by a principal point at spot lensing converges at a focal point 3628 that is located at a distance beyond the target (chemical indicator disc 816) so that the light forms the two individual spots 3616(1) and 3616(2) on the target. In one example, wherein spacing S is about 3.5 mm, the focal distance F to focal point 3628 is about 7.8 mm. In addition, it is noted that spot lensing 3608 is further designed to provide very little to no variance in measurements acquired over a relatively wide range of spacing S. In other words, the amount of light collected by combined I/LC 3600 remains largely unchanged despite spacing S varying due to wobble and/or other factors. This is illustrated, for example, in the graph 3700 of FIG. 37, which shows that there is no more than about 1% variance in measurements over a range of almost 2.0 mm. In graph 3700 of FIG. 37, curve 3704 represents the detected intensity, as a percentage of the maximum intensity, of an illumination spot formed by a combined I/LC similar to combined I/LC 3600 of FIG. 36 using a red LED input. Curve 3708 is a similar curve, but for fluorescent light detected from a spot illuminated using a light of an appropriate excitation wavelength for the particular chemical indicator used. Curve 3712 represents the ratio of (R/Rm)/(F/Fm) where R is reflectivity reading and Rm is maximum Reflectivity reading, F is fluorescence reading and Fm is maximum fluorescence reading. As can be seen from graph 3700, curve 3712 reveals that no more than about 1% variation in intensity occurs over a range 3716 of almost 2.0 mm when using this ratiometric correction step. It should be noted that any number of different wavelengths of light could be used to create this reflectance signal used for correction.

Referring again to FIG. 36, the relative wide range distance S having low intensity variation can be important to the quality of results provided by an aquatic environment water parameter testing system when there is variance in distance S from reading to reading, for example, due to things like movement of a chemical indicator element with respect to the optical reader element. In addition, it is noted that the relatively wide range of allowable error for spacing S allows a designer to carefully choose the size of illumination spots 3616(1) and 3616(2) to control the amount of photo-aging of the particular chemical indicator at issue. Generally, the lower the brightness of the illumination, the slower the photo-aging. Thus, by making illumination spots 3616(1) and 3616(2) relatively large, the intensity of the brightness at any location within that spot is lower than if the same light 3620(1) and 3620(2) were used to form a smaller spot, which would be of greater brightness intensity. That would be the case if the target (a chemical indicator element) were moved closer to focal point 3628, thereby increasing spacing S. That said, over a certain optimal range, despite differences in spacing S, largely the same amount of light is collected from a more-intense smaller spot as is collected from a less-intense larger spot. When spacing S is selected to be in this optimal range, substantial immunity to negative effects of disc wobble and other inaccuracies in spacing S and minimizing photo-aging can be readily accounted for.

Figure 35:
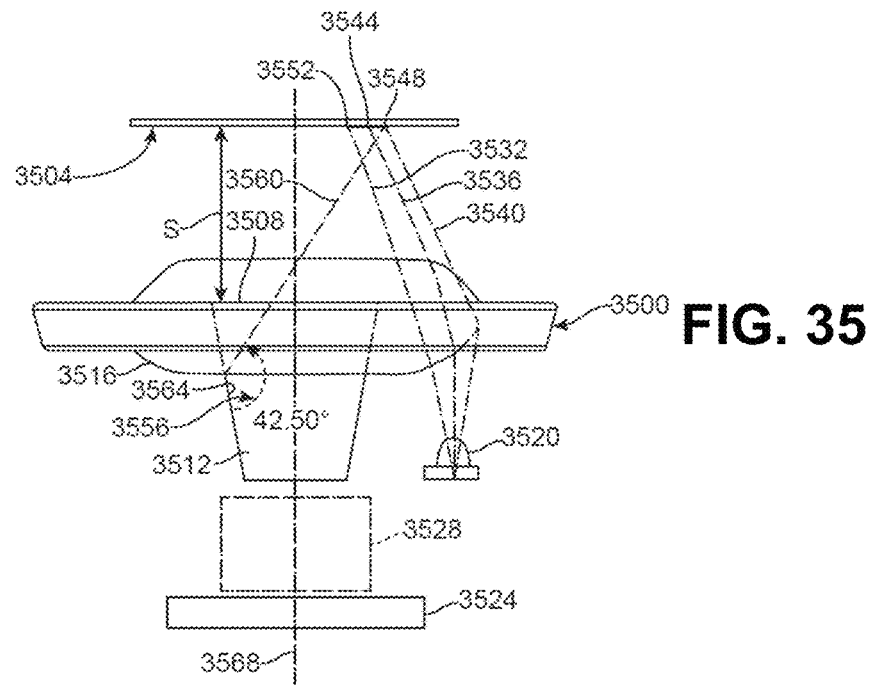
FIG. 35 illustrates a diagram showing exemplary considerations that can be used to design an optical reader element.

FIG. 35 is a diagram illustrating considerations that can be used to design an optical reader element (also referred to as a combined I/LC in this discussion) of the present disclosure. As seen in FIG. 35, which illustrates an I/LC 3500 and a target 3504 (such as a chemical indicator of a chemical indicator element) spaced from the I/LC by distance (spacing) S to an upper portion 3508 of a light collector 3512 that collects light from the target in the manner described above relative to I/LC 3604 of FIG. 36. FIG. 35 also illustrates spot lensing 3516 of I/LC 3500, a light source 3520, a light detector 3524, and an optional light filter 3528. It is noted that each of light source 3520, light detector 3524, and filter 3528 can be the same as or similar to any of the like items described herein. As seen in FIG. 35, the light emitted by light source 3520 is represented by three rays 3532, 3536, and 3540, which represent, respectively, the inside half-brightness flux line, the full brightness flux line, and the outside half-brightness flux line. The light from light source 3520 that is directed onto target 3504 by spot lensing 3516 forms a spot 3544 of light having points 3548 and 3552 that are the outside and inside half-brightness points, respectively. An angle 3556 is the critical angle for the interface of the material of light collector 3512 and air (which here laterally surrounds the light collector). In the present example wherein light collector 3512 is made of acrylic, critical angle 3556 is 42.5°. The ray 3560 leading to critical angle 3556 indicates the angle that is the minimum for the light to be reflected onto detector 3524. Any ray that is less than critical angle 3556 will pass through the side wall 3564 of light collector 3512 and will not reach the detector.

As distance S is increased, the quantity of rays emanating from between outside half-angle point 3548 and inside half-angle point 3552 of spot 3544 that will exceed critical angle 3556 such that they will be directed onto detector 3524 goes up. When the distance S increases, the distance from target 3504 to the aperture formed by the internal TIR center column also increases and therefore results in a reduction of intensity as a function of $1/S^2$. So by balancing the rate in which the rays become less intense due to distance with the rate at which the rays start passing through the sides of light collector 3512 at less than critical angle 3556, a peak detection point can be formed at a desired height with spots 3544 at useful distances from the centerline 3568 of I/LC 3500. By adjusting the angle of side walls 3564 of light collector 3512 relative to centerline 3568, distance S at which the peak light collection occurs can be tuned. The rate at which the light falls off as a functions of distance S change can also be tuned by way of changing whether rays inside and outside half-brightness rays 3532 and 3540 are divergent or convergent as they leave spot lensing 3516 of I/LC 3500. This effectively defines a band of useful operation.

Referring again to FIG. 36, spot lensing 3608 includes a light-entrance surface 3632 that has a high curvature due to the interface of the material of body 3604 with air between light sources 3624(1) and 3624(2) and the need to impart a significant amount of refraction into light 3620(1) and 3620(2) as it proceeds through the spot lensing. In this example, this need is relatively great because the output surface 3636 of spot lensing 3608 interfaces with water, which will typically have an index of refraction that is relatively close to the index of refraction of the material of body 3604 such that little refraction is achievable at surface 3636 without exceedingly drastic curvatures that interfere with other functionality of combined I/LC 3600. It is noted that spot lensing 3608 can be continuous around central light pipe 3612, or not. As an example of the latter, spot lensing 3608 can be notched so that lensing is present only at each light source 3624(1) and 3624(2) and not present therebetween. It is also noted that spot lensing can be provided with one or more contour features at and/or adjacent output surface 3636 that inhibits internal reflection, both partial and total, back into light pipe 3612. Indeed, in the example shown, the curvature at output surface 3636 is configured to direct light coming from light source 3624(2) to pass over-top of light pipe 3612 into spot lensing 3608 on the other side of the light pipe so that it outputs through light-entrance surface 3632 for the opposite light source 3624(1), thereby keeping the stray light from reaching the light pipe and, ultimately, sensor 3660.

In this embodiment, combined I/LC 3600 includes optional laterally dispersive lensing 3640 that acts to direct portions 3644(1) and 3644(2) of the light 3620(1) and 3620(2), respectively, emitted from light sources 3624(1) and 3624(2) away from spots 3616(1) and 3616(2). Directing portions 3644(1) and 3644(2) away from spots 3616(1) and 3616(2), and more generally from the region where light is to be collected by combined I/LC 3600, those portion do not interfere with the readings taken by an optical reader element. Those skilled in the art will readily understand how to design laterally dispersive lensing 3640.

Each light source 3624(1) and 3624(2) can be any suitable source, including filtered and unfiltered monochromatic and multiband light-emitting diodes (LEDs), filtered and unfiltered monochromatic and multiband lasers, filtered and unfiltered incandescent sources, filtered and unfiltered optic fiber(s) in optical communication with a light emitter, etc. Those skilled in the art will understand how to select the proper light source(s) and any optical filter(s) necessary to achieve the desired results.

As for the light collection aspect, combined I/LC 3600 includes central light pipe 3612 that collects light 3648(1)

and 3648(2) from the regions of spots 3616(1) and 3616(2), respectively. As should be apparent from the foregoing discussion, light 3648(1) and 3648(2) can be reflected light from spots 3616(1) and 3616(2) or fluorescent light resulting from the stimulation of any fluorescent dye, for example, from any chemical indicator that includes such dye, from spots 3616(1) and 3616(2), or a combination of both. Central light pipe 3612 include an input end 3652 proximate to chemical indicator disc 816 (when present) and an output end 3656 that directs light 3648(1) and 3648(2) toward one or more suitable optical sensors 3660, which may or may not be located downstream of one or more optional light filters 3664, depending on the sensitivity(ies) of the sensor(s) provided. For example, for a fluorescing dye, it is typically desirable to measure (sense) only the fluorescent light, i.e., without any reflected stimulating light. If the sensor 3660 at issue is a broadband sensor, then it would be desirable to provide one or more filters 3664 that filter out the original stimulating light. Alternatively, if the sensor 3660 at issue is sensitive only to the fluorescent light, then a filter is not needed. It is noted that light pipe 3612 can have any length desired. In such cases, any losses can be accounted for. In this connection, in some embodiments light pipe 3612 can be segmentized, as long as the segments are properly optically coupled. It should also be noted that filters such as evaporated coating dielectric layer filters and other types can be coated onto output end 3656 and become an integral part of the I/LC.

Light pipe 3612 and combined I/LC 3600 more generally include several features to ensure that the light 3648(1) and 3648(2) collected by the light pipe and directed toward sensor(s) 3660 is substantially only light from the target, i.e., chemical indicator disc 816. These features include: the separation of light pipe 3612 from spot lensing 3608 along a portion of the light pipe; the design (curvatures) of entrance and output surfaces 3632 and 3636, respectively, that inhibits internal reflection from spot lensing into light pipe within body 3604; the provision of laterally dispersive lensing 3640; and the design of lateral surface 3668 of the spot lensing that also help inhibit internal reflections from reaching the light pipe. Sensor 3660 can be a surface mounted detector on the bottom side of a printed circuit board (PCB) with a sensing area that collects light through a hole in the PCB. Light sources 3624(1) and 3624(2) can also be surfaces mounted but on the opposite side of the PCB from sensor 3660. This arrangement permits the use of the PCB material to act as a light block for making sure light that is internally scattered from light sources 3624(1) and 3624 (2) can't make direct optical path to sensor 3660.

In the example shown, each light source 3624(1) and 3624(2) comprises a lensed LED package and is located in close proximity to light-entrance surface 3632 of spot lensing 3608. In one example, each light source 3624(1) and 3624(2) output light having a beam angle β of about 10° to about 30°. As used herein and in the appended claims, the term "beam angle" shall mean the angle between the two directions opposed to each other over the beam axis for which the luminous intensity is half that of the maximum luminous intensity of the output of the light source at issue. Depending on the configuration of the reader of which combined I/LC 3600 is part, light sources 3624(1) and 3624(2) can have the same output wavelength(s), or, alternatively, the respective output wavelength(s) can differ from one another. In addition, it is noted that depending on the spectral output of each light source 3624(1) and 3624(2), one, the other, or both can be provided with one or more light filters 3672(1) and 3672(2), respectively, as needed to suit the needs of use.

Figure 38:
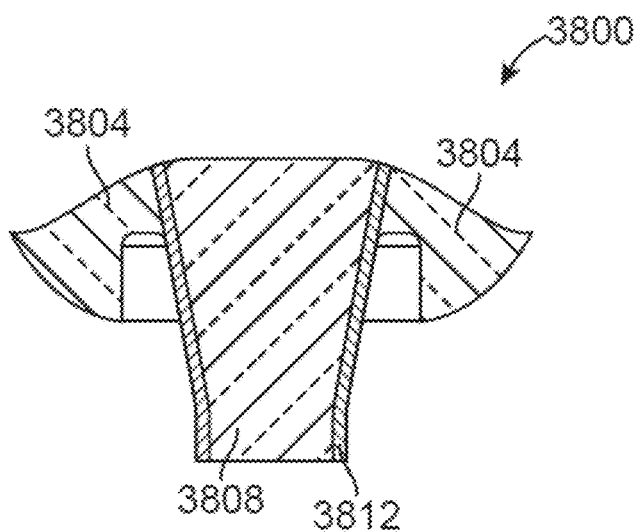
FIG. 38 illustrates another example of an optical reader element.

Whereas FIG. 36 illustrates an example in which combined I/LC 3600 is made in a unitary monolithic manner, FIG. 38 illustrates an alternative optical reader element 3800 (also referred to as a combined I/LC 3800 in this discussion) that is an assembly of multiple separately manufactured parts. Like combined I/LC 3600 of FIG. 36, combined I/LC 3800 of FIG. 38 includes spot lensing 3804 and a central light pipe 3808, each having the same functionality described above for like portions of combined I/LC 3600 of FIG. 36. However, in FIG. 38, light pipe 3808 is formed as a separate component relative to spot lensing 3804. The two components, i.e., light pipe 3808 and spot lensing 3804 are held together, for example, by press fit, with an intermediate sleeve 3812 that separates the light pipe and spot lensing. Intermediate sleeve 3812 is made of any suitable material, such as an opaque material, highly reflective (e.g., mirror-like) material, or a material having an index of refraction suitably different from the materials of light pipe 3808 and spot lensing 3804 such that light internal to each of the light pipe and spot lensing is inhibited from reaching the other component. It is noted that in this example, laterally dispersive lensing (e.g., like laterally dispersive lensing 3640 of combined I/LC 3600 of FIG. 36) is not present. However, in alternative embodiments it can be provided, for example, in a unitary monolithic manner with spot lensing 3804.

It is to be noted that the aspects and embodiments described herein may be conveniently implemented using one or more machines (e.g., one or more computing devices/computer systems that are part of an aquatic environment monitoring and/or dosing system) including hardware and special programming according to the teachings of the present specification, as will be apparent to those of ordinary skill in the computer art. Appropriate software coding can readily be prepared by skilled programmers based on the teachings of the present disclosure, as will be apparent to those of ordinary skill in the software art. For example, one or more aspects, features, and/or embodiments may be implemented using circuitry of an electronics portion of an aquatic environment water parameter testing system, such as electronics portion 305 shown in FIG. 3. In another example, one or more aspects, features, and/or embodiments may be implemented in a machine that is connected (e.g., via a network connection) to an electronics portion of an aquatic environment water parameter testing system, such as electronics portion 305.

Such software may be a computer program product that employs a machine-readable hardware storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable hardware storage medium include, but are not limited to, a magnetic disk (e.g., a conventional floppy disk, a hard drive disk), an optical disk (e.g., a compact disk "CD", such as a readable, writeable, and/or re-writable CD; a digital video disk "DVD", such as a readable, writeable, and/or rewritable DVD), a magneto-optical disk, a read-only memory "ROM" device, a random access memory "RAM" device, a magnetic card, an optical card, a solid-state memory device (e.g., a flash memory), an EPROM, an EEPROM, and any combinations thereof. A machine-readable medium, as used herein, is intended to include a single medium as well as a collection of physically separate media, such as, for example, a collection of compact disks or one or more hard disk drives in combination with a computer memory. As used herein, a machine-readable storage medium does not include a signal. As discussed above, an aquatic environment water parameter testing system of the present disclosure may include a memory reader device, such as a memory card reader. It is also noted, that an aquatic environment water parameter testing system of the present disclosure may also have one or more other memory elements (e.g., configured to communicate with a processing element of an aquatic environment water parameter testing system) for storing software and/or information (e.g., data, equations, relationships, etc.) for carrying out any one or more of the aspects, features, and/or embodiments discussed above with respect to the various implementations of an aquatic environment water parameter testing system.

Such software may also include information (e.g., data) carried as a data signal on a data carrier, such as a carrier wave. Such a data signal or carrier wave would not be considered a machine-readable hardware storage medium. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronics portion of an aquatic environment water parameter testing system, a computer workstation, a terminal computer, a server computer, a handheld device (e.g., tablet computer, a personal digital assistant "PDA", a mobile telephone, etc.), a web appliance, a network router, a network switch, a network bridge, any machine capable of executing a sequence of instructions that specify an action to be taken by that machine, and any combinations thereof. In one example, a computing device may include and/or be included in, a kiosk. In another example, a dosing calculator (as discussed herein) may be associated with (e.g., be part of, be connected to, be included in, etc.) a computing device or any part thereof.

Figure 39:
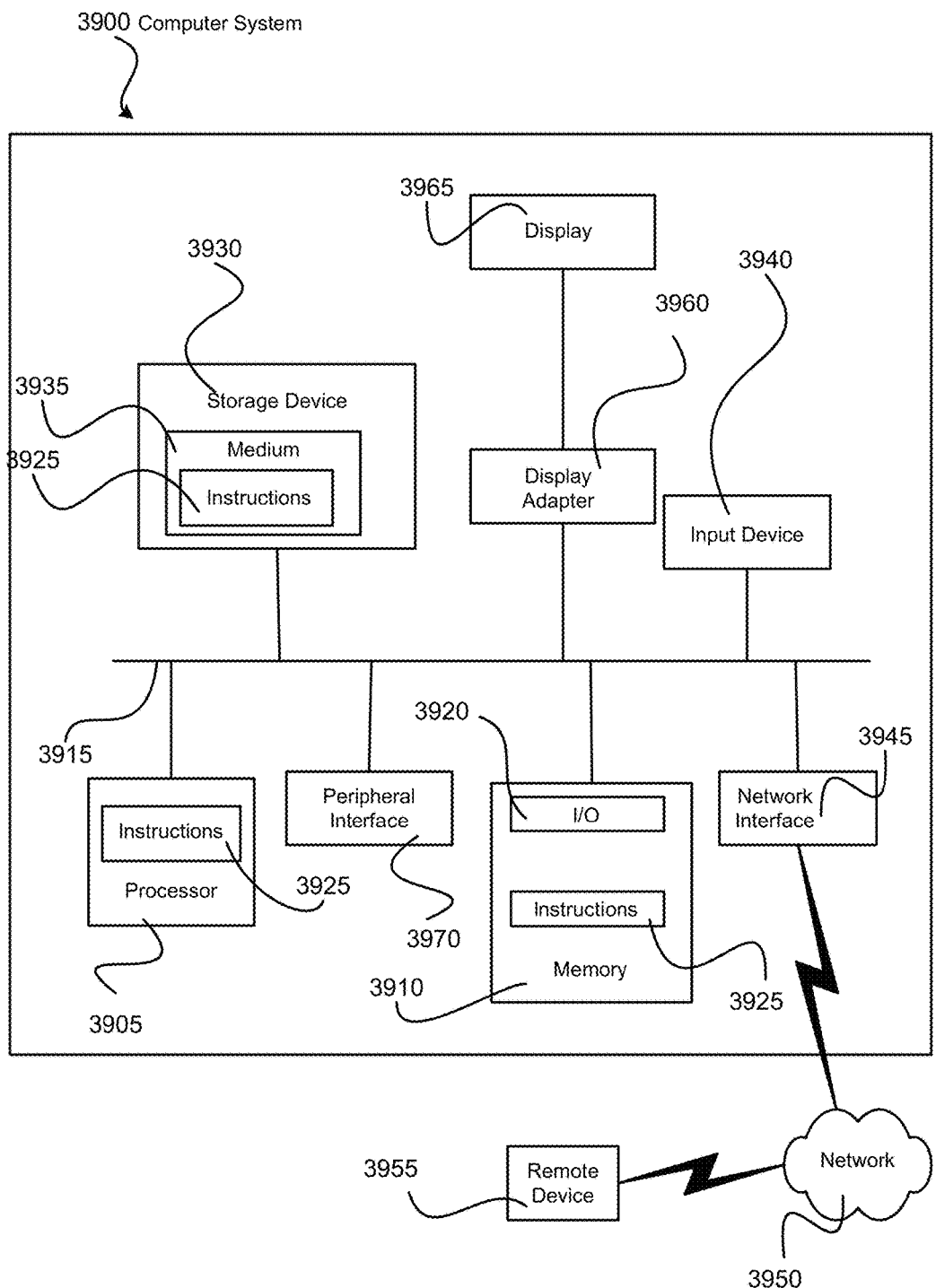
FIG. 39 illustrates a diagrammatic representation of one exemplary embodiment of a computing system.

FIG. 39 shows a diagrammatic representation of one exemplary embodiment of a computing system 3900, within which a set of instructions for causing one or more processors 3904 to perform any one or more of the functionalities, aspects, and/or methodologies of the present disclosure. It is also contemplated that multiple computing device may be utilized to implement a specially configured set of instructions for performing any one or more of the functionalities, aspects, and/or methodologies of the present disclosure in a distributed computing matter. It is also contemplated that a computing device may omit any one or more of the components of computing system 3900.

Computing system 3900 can also include a memory 3908 that communicates with the one or more processors 3904, and with other components, for example, via a bus 3912. Bus 3912 may include any of several types of bus structures including, but not limited to, a memory bus, a memory controller, a peripheral bus, a local bus, and any combinations thereof, using any of a variety of bus architectures.

Memory 3908 may include various components (e.g., machine-readable hardware storage media) including, but not limited to, a random access memory component (e.g., a static RAM "SRAM", a dynamic RAM "DRAM", etc.), a read only component, and any combinations thereof. In one example, a basic input/output system 3916 (BIOS), including basic routines that help to transfer information between elements within computing system 3900, such as during start-up, may be stored in memory 3908. Memory 3908 may also include (e.g., stored on one or more machine-readable hardware storage media) instructions (e.g., software) 3920 embodying any one or more of the aspects and/or methodologies of the present disclosure. In another example, memory 3908 may further include any number of program modules including, but not limited to, an operating system, one or more application programs, other program modules, program data, and any combinations thereof.

Computing system 3900 may also include a storage device 3924, such as, but not limited to, the machine readable hardware storage medium described above. Storage device 3924 may be connected to bus 3912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 3924 (or one or more components thereof) may be removably interfaced with computing system 3900 (e.g., via an external port connector (not shown)). Particularly, storage device 3924 and an associated machine-readable medium 3928 may provide nonvolatile and/or volatile storage of machine-readable instructions, data structures, program modules, and/or other data for computing system 3900. In one example, software instructions 3920 may reside, completely or partially, within machine-readable hardware storage medium 3928. In another example, software instructions 3920 may reside, completely or partially, within processors 3904.

Computing system 3900 may also include an input device 3932. In one example, a user of computing system 3900 may enter commands and/or other information into computing system 3900 via one or more input devices 3932. Examples of an input device 3932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), touch screen, and any combinations thereof. Input device(s) 3932 may be interfaced to bus 3912 via any of a variety of interfaces (not shown) including, but not limited to, a serial interface, a parallel interface, a game port, a USB interface, a FIREWIRE interface, a direct interface to bus 3912, and any combinations thereof. Input device(s) 3932 may include a touch screen interface that may be a part of or separate from display(s) 3936, discussed further below. Input device (s) 3932 may be utilized as a user selection device for selecting one or more graphical representations in a graphical interface as described above.

A user may also input commands and/or other information to computing system 3900 via storage device 3924 (e.g., a removable disk drive, a flash drive, etc.) and/or network interface device(s) 3940. A network interface device, such as any one of network interface device(s) 3940 may be utilized for connecting computing system 3900 to one or more of a variety of networks, such as network 3944, and one or more remote devices 3948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network, a telephone network, a data network associated with a telephone/voice provider, a direct connection between two computing devices, and any combinations thereof. A network, such as network 3944, may employ a wired and/or a wireless mode of communication. In general, any network topology may be used. Information (e.g., data, software instructions 3920, etc.) may be communicated to and/or from computing system 3900 via network interface device(s) 3940.

Computing system 3900 may further include one or more video display adapter 3952 for communicating a displayable image to one or more display devices, such as display device(s) 3936. Examples of a display device include, but are not limited to, a liquid crystal display (LCD), a cathode ray tube (CRT), a plasma display, a light emitting diode (LED) display, and any combinations thereof. Display adapter(s) 3952 and display device(s) 3936 may be utilized in combination with processor(s) 3904 to provide a graphical representation of a utility resource, a location of a land parcel, and/or a location of an easement to a user. In addition to a display device, computing system 3900 may include one or more other peripheral output devices including, but not limited to, an audio speaker, a printer, and any combinations thereof. Such peripheral output devices may be connected to bus 3912 via a peripheral interface 3956. Examples of a peripheral interface include, but are not limited to, a serial port, a USB connection, a FIREWIRE connection, a parallel connection, and any combinations thereof.

The systems, methods, apparatuses, software, etc. of the present invention have been exemplified by various exemplary embodiments and implementations as shown in the accompanying drawings and as described above. However, it should be understood that the discrete presentation of these embodiments and implementations should not be construed as requiring that: 1) these embodiments and implementations stand in isolation from one another; 2) that individual components, features, aspects, and/or functionalities described relative to each one of the embodiments and implementations cannot be used independently of the corresponding embodiment or implementation; and 3) that individual components, features, aspects, and/or functionalities described cannot be used individually in connection with other embodiments and implementations, either described herein or derivable therefrom, alone and/or in any combination with one another. On the contrary, those skilled in the art will appreciate that the individual components, features, aspects, and functionalities of a particular embodiment or implementation can, as appropriate under the circumstances, be utilized alone and in any subcombination with other components, features, aspects, and/or functionalities of that particular embodiment or implementation and with any other embodiment or implementation, including the specific examples described herein in connection with FIGS. 1 through 39.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed:

1. A chemical indicator element for use in an aquatic environment water parameter testing system having a light source capable of generating an excitation energy and a light sensor for detecting light, the chemical indicator element comprising:
   a chemical indicator responsive to a first excitation energy to generate a first emitted energy in response to the first excitation energy;
   a backing material that absorbs one or more wavelengths of light of the first excitation energy; and
   a thin film material positioned proximate the chemical indicator between the chemical indicator and the backing material, the thin film material being configured to:
      absorb and/or allow transmission of one or more wavelengths of light of the first excitation energy, and
      reflect one or more wavelengths of light of the first emitted energy.

2. A chemical indicator element according to claim 1, further comprising a holder positioned adjacent a side of the backing material that is opposite the thin film material.

3. A chemical indicator element according to claim 1, further comprising a holder positioned adjacent a side of the chemical indicator that is opposite the thin film material, the holder including a material that allows transmission of the first excitation energy.

4. A chemical indicator element according to claim 1, further comprising a holder positioned adjacent a side of the thin film material opposite to the chemical indicator, the holder including a material that absorbs one or more wavelengths of light of the first excitation energy.

5. A chemical indicator element according to claim 1, wherein the thin film material transmits light with a wavelength below about 490 nm such that about 10 percent of light with a wavelength below about 490 nm is reflected and the thin film material reflects about 80 percent of light having a wavelength of 520 nm and above.

6. A chemical indicator element according to claim 1, wherein the thin film material has a reflectivity profile with a narrow band of reflectivity including a wavelength of light of the first emitted energy and a narrow band of absorption and/or transmission including a wavelength of light of the first excitation energy.

7. A chemical indicator element according to claim 1, wherein the chemical indicator element is part of a sample chamber portion of an aquatic environment water parameter testing system, the aquatic environment water parameter testing system having an optical reader element positioned opposite the chemical indicator element such that a light from the optical reader element is directed at the chemical indicator at a side of the chemical indicator opposite the thin film material and light emitted from the chemical indicator is readable by the optical reader element.

8. A chemical indicator element according to claim 1, wherein the chemical indicator element is configured to be removably attached to a sample chamber portion of an aquatic environment water parameter testing system, the aquatic environment water parameter testing system having an optical reader element positioned opposite the chemical indicator element such that a light from the optical reader element is directed at the chemical indicator at a side of the chemical indicator opposite the thin film material and light emitted from the chemical indicator is readable by the optical reader element.

9. A chemical indicator element according to claim 1, wherein the chemical indicator element is configured to be removably attached to an aquatic environment water parameter testing system, the aquatic environment water parameter testing system having an optical reader element positioned opposite the chemical indicator element such that a light from the optical reader element is directed at the chemical indicator at a side of the chemical indicator opposite the thin film material and light emitted from the chemical indicator is readable by the optical reader element.

10. A chemical indicator element for use in an aquatic environment water parameter testing system having a light source capable of generating an excitation energy and a light sensor for detecting light, the chemical indicator element comprising:
- a chemical indicator responsive to a first excitation energy to generate a first emitted energy in response to the first excitation energy;
- a first holder including a material that absorbs one or more wavelengths of light of the first excitation energy; and
- a thin film material positioned proximate the chemical indicator between the chemical indicator and the first holder, the thin film material being configured to:
  - absorb and/or allow transmission of one or more wavelengths of light of the first excitation energy, and
  - reflect one or more wavelengths of light of the first emitted energy.

11. A chemical indicator element according to claim 10, wherein the thin film material transmits light with a wavelength below about 490 nm such that about 10 percent of light with a wavelength below about 490 nm is reflected and the thin film material reflects about 80 percent of light having a wavelength of 520 nm and above.

12. A chemical indicator element according to claim 10, wherein the thin film material has a reflectivity profile with a narrow band of reflectivity including a wavelength of light of the first emitted energy and a narrow band of absorption and/or transmission including a wavelength of light of the first excitation energy.

13. A chemical indicator element according to claim 10, wherein the chemical indicator element is part of a sample chamber portion of an aquatic environment water parameter testing system, the aquatic environment water parameter testing system having an optical reader element positioned opposite the chemical indicator element such that a light from the optical reader element is directed at the chemical indicator at a side of the chemical indicator opposite the thin film material and light emitted from the chemical indicator is readable by the optical reader element.

14. A chemical indicator element according to claim 10, wherein the chemical indicator element is configured to be removably attached to a sample chamber portion of an aquatic environment water parameter testing system, the aquatic environment water parameter testing system having an optical reader element positioned opposite the chemical indicator element such that a light from the optical reader element is directed at the chemical indicator at a side of the chemical indicator opposite the thin film material and light emitted from the chemical indicator is readable by the optical reader element.

15. A chemical indicator element according to claim 10, further comprising a backing material, the backing material positioned adjacent a side of the thin film material opposite the chemical indicator, the backing material being a material that absorbs one or more wavelengths of light of the first excitation energy.

16. A chemical indicator element according to claim 15, further comprising a second holder positioned adjacent a side of the chemical indicator that is opposite the thin film material, the second holder including a material that allows transmission of the first excitation energy.

17. A chemical indicator element according to claim 1, wherein the chemical indicator is supported on a substrate.

18. A chemical indicator element according to claim 17, wherein the chemical indicator is immobilized in a hydrogel material.

19. A chemical indicator element according to claim 10, wherein the chemical indicator is supported on a substrate.

20. A chemical indicator element according to claim 19, wherein the chemical indicator is immobilized in a hydrogel material.

* * * * *